US012697422B2

(12) United States Patent
Nagy-Gannon et al.

(10) Patent No.: US 12,697,422 B2
(45) Date of Patent: Aug. 4, 2026

(54) BREAST PUMP

(71) Applicant: National University of Ireland, Galway, Galway (IE)

(72) Inventors: Eva Nagy-Gannon, Galway (IE); Sandra Ganly, Galway (IE); Yuqi Shaughnessy, Galway (IE); Faisal Sharif, Galway (IE); Genevieve Becker, Galway (IE); Roy Phillip, Limerick (IE); Migle Dominica Make-Lyte, Galway (IE); Morven Gannon, Galway (IE); Kealan Devlin, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 849 days.

(21) Appl. No.: 17/906,544

(22) PCT Filed: Mar. 18, 2021

(86) PCT No.: PCT/EP2021/057031
§ 371 (c)(1),
(2) Date: Sep. 16, 2022

(87) PCT Pub. No.: WO2021/186006
PCT Pub. Date: Sep. 23, 2021

(65) Prior Publication Data
US 2023/0173148 A1 Jun. 8, 2023

(30) Foreign Application Priority Data
Mar. 19, 2020 (EP) .................................... 20164358

(51) Int. Cl.
*A61M 1/06* (2006.01)

(52) U.S. Cl.
CPC ........ *A61M 1/064* (2014.02); *A61M 1/06935* (2021.05); *A61M 1/0697* (2021.05); *A61M 2205/106* (2013.01)

(58) Field of Classification Search
CPC ........................ A61M 1/06935; A61M 1/0697
See application file for complete search history.

(56) References Cited

U.S. PATENT DOCUMENTS 1,048,481 A * 12/1912 Aslakson .................. A01J 5/08
119/14.52
6,383,163 B1 5/2002 Kelley et al.
(Continued)

FOREIGN PATENT DOCUMENTS

CN 2246517 Y 2/1997
CN 2827382 Y 10/2006
(Continued)

OTHER PUBLICATIONS

International Search Report and Written Opinion for International Appl. No. PCT/EP2021/057031, entitled "Breast Pump", consisting of 16 pages. Date Mailed: Jun. 7, 2021.

*Primary Examiner* — Nathan R Price
(74) *Attorney, Agent, or Firm* — HAMILTON, BROOK, SMITH & REYNOLDS, P.C.

(57) ABSTRACT
A biomechanical breast pump mechanism (1) for expressing breastmilk comprising a biomimetic funnel (2), at least two active actuation areas (23,24) on the funnel (2) and stationary areas (25), the active actuation areas (23,24) being actuatable by a driving mechanism or mechanisms (3) and being configured to replicate the complex functions of the infant's tongue during suckling namely the physical stimulation of the areola (17)/nipple (16); nipple positioning; creating and maintaining low-level baseline vacuum to create air-seal on the breast; generating sub-atmospheric pressure inside the funnel (2); creating and maintaining
(Continued)

close-to-zero-air environment in the funnel (2); and control of the vacuum oscillation within predefined ranges coordinated negative and positive actuation (41,42) of one or both actuation areas (23,24) independently or simultaneously.

12 Claims, 18 Drawing Sheets

(56)                    References Cited

U.S. PATENT DOCUMENTS

| | | | |
|---|---|---|---|
| 7,758,540 | B2 | 7/2010 | Yamashita et al. |
| 2005/0234400 | A1 | 10/2005 | Onuki |
| 2014/0330200 | A1 | 11/2014 | Scheidegger et al. |
| 2015/0065994 | A1* | 3/2015 | Fridman ............. A61M 1/0697 |
| | | | 604/74 |
| 2015/0217037 | A1 | 8/2015 | Pollen et al. |
| 2017/0006573 | A1 | 1/2017 | Kelly |
| 2017/0072118 | A1 | 3/2017 | Makower et al. |
| 2017/0173235 | A1 | 6/2017 | Alvarez et al. |

FOREIGN PATENT DOCUMENTS

| | | | |
|---|---|---|---|
| CN | 201171817 | Y | 12/2008 |
| CN | 201370808 | Y | 12/2009 |
| CN | 106377809 | A | 8/2017 |
| EP | 2 111 882 | A1 | 10/2009 |
| WO | 20160014469 | A1 | 1/2016 |
| WO | 2018229782 | A1 | 12/2018 |

* cited by examiner

BREAST PUMP

This application is the U.S. National Stage of International Application No. PCT/EP2021/057031, filed Mar. 18, 2021, which designates the U.S., published in English, and claims priority under 35 U.S.C. § 119 or 365(c) to European Application No. 20164358.2, filed Mar. 19, 2020. The entire teachings of the above applications are incorporated herein by reference.

INTRODUCTION

This invention relates to a biomechanical breast pump for expressing breastmilk and to a method of expressing breastmilk.

BACKGROUND OF THE INVENTION

The use of breast pumps by nursing mothers to express breastmilk is widely known and various breast pumps and systems have been developed in which a negative/sub-atmospheric pressure is applied to the breast to express the breastmilk which is then collected in a container attached to the breast pump. Most breast pumps are piston pumps, fast-diaphragm pumps, slow-diaphragm pumps or similar state of the art technologies which generate vacuum, which is then channeled into a breast shield where the nipple is positioned. More recent solutions use piezo pumps (WO 2018/229504A1), mechanical drivers (US 2016/0206794A1) or hydraulic, pneumatic technology (US 2019/0151521A1, US 2018/0154055, US2018/078687A1) to generate a vacuum.

However, despite the availability of known breastmilk pumps, it can still be difficult for nursing mothers to express breastmilk when using breastmilk pumps while the use of such pumps can cause discomfort.

There is an increasing understanding and attention being given to replicating an infant's suckling action for the benefits of comfort and efficiency. The specifics of the infant's suckling profile and the role of the tongue in it are becoming more evident. More particularly, infant suckling comprises a range of functions that must all be present to achieve the most comfortable and efficient way of drawing milk from the breast. These include:

physical stimulation of the nipple/areola to trigger a milk ejection reflex (MER);
    close-to-zero-air environment in the intra-oral cavity where the nipple is positioned;
    generating sub-atmospheric pressure at a certain frequency and strength;
    and maintaining a continuous baseline, low vacuum level to keep a continuous air-seal on the nipple/areola/breast during suckling.

The infant uses his tongue to generate these functions and to coordinate and control the complexity of them for maximum efficiency and comfort. This makes the tongue the key driver of suckling. Accurately replicating all these functions is the key to achieving the most comfortable and efficient way to express milk. Commercial breast pumps have technological limitations so that when technologies are labelled biomimetic with regards to replicating the suckling action of the infant, their capability is limited to replicating some but not all of the abovementioned functions.

For example, commercial breast pumps of the prior art as outlined above such as piston or diaphragm or piezo pumps can control the speed, frequency, and strength of the vacuum pressure. This means that they can replicate one function of the complex suckling mechanism namely the generation of sub-atmospheric pressure at similar speed, frequency, and strength as a suckling infant. However, due to the limitations of the technology, they are not capable of recreating the rest of the suckling functions and often use higher vacuum pressures to compensate for the lack of similarity, which can result in increased discomfort for the user.

Some breast pumps aim to alleviate discomfort by introducing soft inserts and/or soft shields. This way the delicate breast tissue is not in direct contact with the rigid plastic shield, alleviating some of the discomfort caused by pressure from the rigid pieces. Other solutions go further and shape the soft shields/inserts in a way that the pliability of these soft shields causes the shield to collapse under peak sub-atmospheric pressure onto the breast/areola/nipple which would create compression stimulation on the breast/nipple/areola to replicate the physical stimulation exerted by the tongue of the suckling infant (U.S. 63/831,6361, US 2019/209750A1, US2020/0405925). This way these shields not only improve comfort but fulfil a second function of the tongue, which is to trigger MER. However, they remain limited in the level of controllability necessary to accurately replicate the physical stimulation function of the tongue. In the case of these designs the compression can only happen when vacuum level is peaking, which is not the case in the infant's suckling profile, e.g., compression and peak vacuum does not always happen at the same time.

The physical effect the tongue has on the areola and the base of the nipple are crucial factors in fluid expression. Thus, traditional breast pumps are far from biomimetic/biomechanical and are low in efficacy at evoking the milk ejection response (MER) in nursing women.

WO 2018/229782A1 uses a roller under the areola/nipple to create a circular arc motion and with that a rhythmical compression on that area. A similar effect is achieved by US 2005/234400A1 and EP 2111882A1 that use a set of plates that are pushed into the soft membrane at the lower part of the soft breast shield, coordinated into a wave-like sequence. However, these devices still rely on a separate vacuum unit to generate sub-atmospheric pressure and run into the same limitations as conventional vacuum pumps. In addition, at best, these solutions can recreate only two functions of the complex suckling mechanism: vacuum generation from the separate vacuum unit and compression stimulation on the breast/nipple/areola to trigger MER.

The mechanical solution of US2016/0206794A1 resembles the biomechanical method that the infant is using to generate vacuum in its intra-oral cavity, in a way that it is mechanically increasing the volume of space in an airtight chamber like the tongue does. US2016/0206794A1 vacuum generating method is based on the rebounding properties of the material of the tube section which is compressed and then released. As it rebounds it generates vacuum within the tube. By controlling the level of release a continuous low vacuum level can also be maintained. In this respect this solution recreates the following functions of the suckling mechanism: generates vacuum, creates, and maintains a close-to-zero-air environment inside the tube, and maintains a baseline vacuum level during pumping.

US2019/0151521A1 is a hydraulic/pneumatic solution that includes a first and a second hermetic expandable and contractible bladder in contact with the bottom portion of the funnel. The limitation of the technology is that only one bladder can be actuated at any given time, while at certain points in the suckling cycle the infant moves the anterior and posterior part of his tongue in the opposite direction which is necessary for achieving the full range of functions of the suckling mechanism. Due to the arrangement of the bladders, the system either compromises its ability to maintain continuous baseline vacuum or compromises its ability to apply compression stimulation. If it maintains a baseline vacuum level, then it won't be able to achieve full compression with the first bladder.

In summary, known breastmilk pumps that attempt to replicate a suckling infant still suffer from a number of disadvantages. For example, when known sub-atmospheric pressure pumping technologies are labelled biomimetic with regards to geometry and action of an infant's intra-oral cavity, it is only usually a single aspect of the biological system that is being addressed—e.g. the applied sub-atmospheric pressure is defined by frequency, strength and acceleration only and key components of a true biomimetic/biomechanical system are disregarded. For example, generally, sub-atmospheric pressure is generated when the posterior area of the infant's tongue descends and stimulation is carried out by the anterior part of the tongue by applying compression to the areola and/or the base of the nipple. The physical effect the tongue has on the areola and the base of the nipple are crucial factors in fluid expression. Thus, traditional breast pumps are far from biomimetic/biomechanical and are low in efficacy at evoking the milk ejection response (MER) in nursing women. Some known breastmilk pumps also offer soft breast shields for added comfort during use. However, the pliability of these soft shields can cause the shield to collapse under peak sub-atmospheric pressure inducing a compression on the breast and areola. Most known breast pumps are inefficient compared to an infant's suckling action and, despite improvements in design, cause discomfort. For example, known breastcup or funnel structures (hereinafter referred to as funnels) and associated tubes are rigid thus giving rise to dead air volumes resulting in maximum negative pressures of between about −200 and −300 mm Hg which results in increased pressures being required to express liquid together with increased discomfort for the user caused by tugging on the nipple by the funnel. This pulling action can also restrict flow in lactiferous ducts while the relatively large rigid funnels of the prior art can also exert excessive pressure on adjacent sensitive breast tissue.

Accordingly, known breast pumps fail to adequately replicate all of the functions of the infant's suckling mechanism.

An object of the invention is to overcome at least some of the problems of the prior art.

SUMMARY OF THE INVENTION

In its broadest sense, the invention relates to a biomechanical breastmilk pump for expressing breastmilk comprising:
  a biomimetic funnel, and
  at least two active actuation areas on the funnel,
the active actuation areas being actuatable by an actuator or actuators and being configured to mimic an infant's tongue during suckling.

According to the invention there is provided a biomechanical breast pump for expressing breastmilk comprising:
  a biomimetic funnel formed from a deformable body having a lip end, a milk discharge end and a wall extending between the lip end and the discharge end;
  at least two active actuation areas on the deformable body configured to mimic an infant's complex suckling function;

a stationary actuation area on the deformable body configured to stop a hard palate defined in the deformable body from deforming in response to movement of the active actuation areas, and
an actuator or actuators for actuating the active actuation areas wherein the active actuation areas are independently and/or simultaneously actuatable by the actuator or actuators to exert a positive or negative actuation force on the deformable body.

Suitably, the active actuation areas are provided on a lower soft floor of the deformable body and the stationary actuation area is provided at an oppositely disposed relatively hard upper palate of the deformable body.

Preferably, the deformable body defines lips and a nipple chamber fluidly communicable with the lips to mimic the geometry of an infant's oral cavity and a milk discharge end.

In a preferred embodiment, the active actuation areas comprise an anterior actuation area disposed towards the lip end and a posterior actuation area disposed towards the milk discharge end.

Advantageously, the anterior actuation area is configured to stimulate the areola and/or the nipple of a user and to keep the nipple in position.

In one embodiment, the actuation areas are defined by the material of the deformable body.

Preferably, the actuator or actuators are operable in response to instructions from a controller to exert a positive actuation force on the active actuation areas towards the stationary actuation area and a negative actuation force on the active actuation areas away from the stationary actuation area and the actuation forces applied to each actuation area can be the same or different. More preferably, the positive actuation force and negative actuation force on the active actuation areas are actuatable by the actuator or actuators in response to instructions from the controller in accordance with key variables selectable from the group comprising or consisting of but not limited to origin point 38 of the active actuation areas; travel distance of the active actuation areas along the trajectory of actuation; travel direction positive or negative; travel direction of the active actuation areas; angle of travel of the active actuation areas; actuation sequence of the active actuation areas independently and in relation to each other; frequency, velocity, acceleration, deceleration and timing of one suckling cycle within a suckling programme, and frequency, velocity, acceleration, deceleration and timing of a single actuation within one suckling cycle.

In a preferred embodiment, the nipple chamber comprises a proximal nipple zone positioned between the anterior actuation area and the posterior actuation area and a distal pharynx.

In any embodiment, the biomechanical breast pump further comprises at least one drivetrain extending between the actuator or actuators and the active actuation areas.

Preferably, the drivetrain is connected to the anterior and posterior actuation areas via an actuation body disposed on the outer face of the funnel wall.

Advantageously, the breast pump comprises an anterior actuation body and a posterior actuation body.

In any embodiment, the anterior and posterior actuation bodies positionally correspond with the anterior and posterior active actuation areas.

Optionally, the anterior and posterior actuation bodies are attachable to and detachable from the drivetrain at drivetrain pads. Advantageously, the internal faces of the pads comprise ridges/grooves 80 to improve contact with the actuation bodies. Suitably, the pads are formed from a hard plastics or other hard material so that the ridges/grooves can be pressed into the anterior and posterior actuation bodies.

In one embodiment, the anterior and posterior actuation bodies comprise inserts or overmoulds. Suitably, the inserts or overmoulds are connected to the drivetrains via a link pin extending between the drive trains and a link pin opening 83 defined in the inserts or overmoulds.

In any embodiment, the funnel wall comprises an anatomical and/or suckling replicator and/or a fluid discharge enhancer.

Preferably, the anatomical and/or suckling replicator comprises a nipple base stimulator on the internal funnel wall over the anterior active actuation area.

Optionally, the nipple base stimulator is bump-like or has a half cylindrical arc shape.

Alternatively or in addition, the anatomical and/or suckling replicator comprises a funnel closing or sealing body on the funnel wall.

In another embodiment, the funnel comprises a structural reinforcer.

Optionally, the structural reinforcer comprises a side reinforcer on the funnel wall.

Preferably, the side reinforcer is an elongate side reinforcer disposed on the external funnel wall. More preferably, the side reinforcer has a triangular cross-section. Alternatively, the side reinforcer has a square cross-section.

Advantageously, the side reinforcer comprises an elongate slit and the reinforcer is movable between a flexed open and a flexed closed position about the slit.

In another embodiment, the structural reinforcer comprises a nipple chamber reinforcer. Preferably, the nipple chamber reinforcer comprises a ring around the funnel.

In another embodiment, the structural reinforcer comprises a nipple mouth reinforcer.

In another embodiment, the structural reinforcer comprises a lip reinforcer.

Preferably, the lip reinforcer comprises elongate ribs extending from the lips.

In another embodiment, the structural reinforcer comprises a discharge end reinforcer.

Preferably, the discharge end reinforcer is provided on a one-way valve the discharge end. More preferably, the discharge end reinforcer comprises a reinforcing band on one way valve.

In another embodiment, the fluid discharge enhancer comprises a milk driving replicator on the internal funnel wall. Preferably, the milk driving replicator is disposed over the posterior active actuation area.

In any embodiment, the anatomical and/or suckling replicators and the structural reinforcers are formed by protrusions in the funnel wall.

In one embodiment of the invention, the lips are configured to define an underbite.

In another embodiment of the invention, the lips are configured to define an open V-shape in profile.

In another embodiment, the lips are configured to define a closed V-shape in profile. In any embodiment of the invention, the actuator is a two-way actuator.

Optionally, the actuator comprises an electromechanical motor, a servo motor, a stepper motor, a piston, a lever arm, an electromagnetic motor, a linear driver, a solenoid, a gear, a pneumatic drive or a hydraulic drive.

In another embodiment of the invention, the actuator comprises a manually operated actuator.

Suitably, the manually operated actuator comprises a connector extending from the anterior active actuation area towards the posterior active actuation area.

In another embodiment, the invention extends to a method for operating a biomechanical breast pump having a biomimetic funnel formed from a deformable body;

at least two active actuation areas on the deformable body configured to mimic an infant's complex suckling function;

a stationary actuation area on the deformable body configured to stop a hard palate defined in the deformable body from deforming in response to movement of the active actuation areas, and an actuator or actuators for actuating the active actuation areas, the method comprising exerting a positive actuation force on the active actuation areas towards the stationary area and/or exerting a negative actuation force on the active actuation areas away from the stationary area wherein the positive and negative actuation forces can be independently and/or simultaneously applied to the active actuation areas.

Preferably, the biomechanical breast pump is operated for the purpose of expressing milk to feed a child.

In one embodiment, the method comprises manipulating the actuation areas to replicate the complex functions of the infant's tongue during suckling namely the physical stimulation of the areola/nipple; nipple positioning; creating and maintaining low-level baseline vacuum to create air-seal on the breast; generating sub-atmospheric pressure inside the funnel; creating and maintaining close-to-zero-air environment in the funnel; and control of the vacuum oscillation within predefined ranges.

Suitably, the active actuation areas comprise an anterior actuation area disposed towards a lip end of the funnel and a posterior actuation area disposed towards a milk discharge end of the funnel and the method comprises exerting a positive actuation force on the active actuation areas towards the stationary actuation area and a negative actuation force on the active actuation areas away from the stationary actuation area wherein the actuation forces applied to each actuation area are the same or different.

Advantageously, the positive and negative actuation forces are exerted on the active actuation areas in accordance with key variables selectable from the group comprising or consisting of but not limited to: origin point of the active actuation areas; travel distance of the active actuation areas along the trajectory of actuation; travel direction positive or negative; travel direction of the active actuation areas; angle of travel of the active actuation areas; actuation sequence of the active actuation areas independently and in relation to each other; frequency, velocity, acceleration, deceleration and timing of one suckling cycle within a suckling programme, and frequency, velocity, acceleration, deceleration and timing of a single actuation within one suckling cycle.

In another embodiment, the invention extends to a method of expressing breastmilk comprising operating a biomechanical breast pump having a biomimetic funnel formed from a deformable body;

at least two active actuation areas on the deformable body configured to mimic an infant's complex suckling function;

a stationary actuation area on the deformable body configured to stop a hard palate defined in the deformable body from deforming in response to movement of the active actuation areas, and an actuator or actuators for actuating the active actuation areas, the method comprising exerting a positive actuation force on the active actuation areas towards the stationary area and/or exerting a negative actuation force on the active actuation areas away from the stationary area wherein the positive and negative actuation forces can be independently and/or simultaneously applied to the active actuation areas.

Preferably, the biomechanical breast pump is operated for the purpose of expressing milk to feed a child.

In one embodiment, the method comprises manipulating the actuation areas to replicate the complex functions of the infant's tongue during suckling namely the physical stimulation of the areola/nipple; nipple positioning; creating and maintaining low-level baseline vacuum to create air-seal on the breast; generating sub-atmospheric pressure inside the funnel; creating and maintaining close-to-zero-air environment in the funnel; and control of the vacuum oscillation within predefined ranges.

Suitably, the active actuation areas comprise an anterior actuation area disposed towards a lip end of the funnel and a posterior actuation area disposed towards a milk discharge end of the funnel and the method comprises exerting a positive actuation force on the active actuation areas towards the stationary actuation area and a negative actuation force on the active actuation areas away from the stationary actuation area wherein the actuation forces applied to each actuation area are the same or different.

Advantageously, the positive and negative actuation forces are exerted on the active actuation areas in accordance with key variables selectable from the group comprising or consisting of but not limited to: origin point of the active actuation areas; travel distance of the active actuation areas along the trajectory of actuation; travel direction positive or negative; travel direction of the active actuation areas; angle of travel of the active actuation areas; actuation sequence of the active actuation areas independently and in relation to each other; frequency, velocity, acceleration, deceleration and timing of one suckling cycle within a suckling programme, and frequency, velocity, acceleration, deceleration and timing of a single actuation within one suckling cycle.

In another embodiment, the funnel wall comprises a funnel closing or sealing body to ensure that the discharge end is sealed at a compression point to optimise milk expulsion. Suitably, the funnel closing or sealing body comprises an extrusion or protrusions on the sidewall.

Optionally, the breastmilk pump further comprises an external body for compressing the discharge end.

The biomechanical breast pump of the invention improves expression efficiency whilst simultaneously minimising user discomfort. More particularly, the breast pump accurately replicates the complex functions of an infant's tongue during suckling for optimal breast milk expression and comfort—namely effects physical stimulation of the nipple/areola to trigger a milk ejection reflex (MER);

achieves close-to-zero-air environment in the intra-oral cavity where the nipple is positioned;

generates sub-atmospheric pressure at a certain frequency and strength;

facilitates oscillating vacuum levels; keeping the nipple in position throughout the suckling, and maintains a continuous baseline, low vacuum level to keep a continuous air-seal on the nipple/areola/breast during suckling.

The biomechanical breast pump of the invention has a deformable funnel defining lips, a nipple chamber and a milk discharge end configured to replicate the infant's tongue and intra-oral cavity. More particularly, the funnel is biomimetic i.e. is shaped and configured to replicate the structure and function of an infant's mouth, intraoral cavity and tongue through controlled manipulation, meticulously replicating the motion and functions of the suckling tongue especially via the lower wall of the funnel. A nipple zone in which the nipple is approximately is positioned in use is provided in the nipple chamber between the anterior and posterior actuation areas. The nipple zone serves as a comfort zone for the nipple.

The funnel of the invention is in the form of a soft deformable body and the actuation areas serve to effectively replicate an infant's oral cavity and tongue. In particular, the top section of the funnel including the passive/stationary actuation area (hereinafter referred to as a stationary actuation area) replicate an infant's hard palate and ensures that the top part of the funnel remains stationary, i.e. the hard palate is prevented from deforming, during activation of the anterior and posterior active actuation areas. The active actuation areas—the anterior active actuation area and the posterior active actuation area on the lower wall of the deformable body are separately, independently and jointly actuatable and controllable by electromechanical, mechanical or other types of driving mechanisms or actuators operable in response to instructions from a controller (e.g. a microcontroller) to exert a positive actuation force (an active funnel wall inwards or push force—an instroke) and negative actuation force (an active funnel wall outwards or pull force—an outstroke) on the funnel in a bionic and biomimetic fashion via a drivetrain attached to the actuation areas i.e. the actuators exert a positive actuation force towards the stationary actuation area and a negative actuation force away from the stationary actuation area from the active actuation areas of the funnel in a biomechanical and biomimetic fashion via an actuator attached to the funnel via a drivetrain. In alternative embodiments the actuator can be a manual actuator.

The stationary areas are coupled with external stationary bodies positioned on the external side of the funnel at the stationary area to keep the funnel from deforming when actuation is exerted on the corresponding actuation areas. In the preferred embodiment the stationary bodies are part of the upper hard palate of the funnel. The stationary bodies and upper hard palate is the point of contact with the breast pump to keep the funnel stationarily in place during operation while also allowing the funnel to be attachable to and detachable from the breast pump. The anterior actuation area is configured to stimulate the areola and/or nipple and to aid the nipple positioning during pumping. It also contributes to the generation of sub-atmospheric pressure; the control of oscillating vacuum ranges; and the maintaining of the baseline vacuum level to keep air-seal on the breast/areola.

The exact location of the actuation areas are relative to the lip end and milk discharge end as well as relative to each other and are defined by the properties of the material or materials of the funnel as well as the shape and size of the funnel.

The shape, size and functionality of the actuation areas can be defined by the choice and composition of materials of the funnel such as the durometer hardness of the material or other physical anatomical and/or suckling replicators and structural reinforcements such as inserts, extrusions, protrusions, geometrical shapes on the deformable body. The top part of the funnel including the stationary actuation area replicates the hard palate of an infant which remains substantially stationary during actuation, while the active actuation areas are positioned to biomimetically replicate an infant's anterior and posterior part of the tongue during suckling. The material of the funnel can have a durometer hardness between Shore00-20 to about ShoreD-80. Optionally, the funnel comprises a material of single-shore hardness or a combination of materials of different durometer hardness combined together in state of the art method (glue, pressed, molded, overmolded, etc.). In some embodiments, the external actuation bodies comprise inserts in the funnel.

The funnel further comprises anatomical and/or suckling replicators and structural reinforcements on the funnel at locations of geometric value to replicate an infant's intraoral cavity and locations of functional importance to aid or enhance the functions of the complex suckling mechanism. The anatomical and/or suckling replicators and structural reinforcements can locally increase flexibility or increase rigidity or alter the internal or external shape of the funnel at predefined areas. These anatomical and/or suckling replicators and structural reinforcements can take the form of internal or external extrusions, protrusions, changes in geometry, changes in material thickness, affixing different materials together using any state-of-the-art method, or the combination of any of the above. The purpose of these anatomical and/or suckling replicators and structural reinforcements is to aid or enhance the functions of the complex suckling mechanism. The location, shape and size of these anatomical and/or suckling replicators and structural reinforcements can vary among the different embodiments of the funnel and several of these methods can be considered for each anatomical and/or suckling replicator and structural reinforcement within one embodiment as well. One example of such anatomical and/or suckling replicators and structural reinforcements is a stimulator which is placed on the anterior actuation area on the inside of the funnel to enhance the stimulation effect on the areola/nipple. As outlined further below, it can take a form of a half cylindrical arc from the funnel, or a protrusion from the funnel's own material or several other suitable forms. Other examples are the structural reinforcement along the side of the nipple chamber positioned externally on the funnel. The purpose of these reinforcements is to ensure that the funnel has the right level of flexibility for the actuation and the right level of rigidity to remain operable as the vacuum pressure is building up inside it. The reinforcements ensure that this balance between flexibility and rigidity is achieved.

The actuators can be a wide range of suitable drives that can be directly or in translation by the drivetrain used as a minimum two-way actuator. Such example is electromechanical motor, servo motor, stepper motor, piston, lever arm, electromagnets, linear driver, solenoids, gears, pneumatic, hydraulic drives, or other state-of-the-art features. The actuators can further comprise at least one drivetrain extending from the actuator and connecting with the external actuation bodies of the funnel. The drivetrain is designed to be attachable and detachable from the external actuation bodies of the funnel and designed to connect with the external actuation bodies without the risk of losing attachment from either the external actuation bodies or the driving mechanism during actuation.

The active actuation areas are actuatable by the actuator or actuators in response to instructions from the controller to exert positive actuation and negative actuation on the active actuation areas. Positive actuation is defined as the direction when the active actuation area is moving or being moved towards the corresponding stationary area and negative actuation is defined as the direction when the actuation area is moving or being moved away from the corresponding stationary area. Most preferably, the positive actuation and negative actuation on the active actuation areas are actuatable by the actuator or actuators in response to instructions from the controller in accordance with key variables selectable from the group comprising or consisting of but not limited to: origin point of the active actuation area; travel distance of the active actuation area along the trajectory of actuation; displacement direction of the active actuation area; angle of displacement of the active actuation area; actuation sequence of the active actuation areas independently and in coordination with each other; frequency, velocity, acceleration, deceleration and timing of each actuation within one suckling cycle; and frequency, velocity, acceleration, deceleration and timing of each cycle within one suckling programme.

The key variables are selected and defined to generate a range of suckling profile programmes including but not limited to latch, nutritive suckling and non-nutritive suckling profile.

The invention also extends to a breast pump mechanism further comprising a milk container for receiving milk from the breast pump. Preferably, the milk container comprises an air valve.

In one embodiment, the milk container can comprise a pressurised container. In one embodiment, the funnel can comprise lateral actuation areas in addition to the anterior and posterior active actuation areas. The lateral actuation areas can also have external actuation bodies and can perform similar functions to the anatomical and/or suckling replicators and structural reinforcements if desired.

The breastmilk pump can also comprise at least one environmental sensor. Suitably, the environmental sensor comprises a pressure sensor, a fluid flow sensor, a fluid volume sensor, a motion sensor or a temperature sensor or any other sensor deemed necessary to monitor and control any output or input variables observable in the system.

Manipulation of the active actuation areas in accordance with the invention therefore 1. Increases and decreases the volume of space within the deformable body to generate sub-atmospheric pressures similar to those measured in the intra-oral cavity of an infant at similar frequency and speed;
2. Applies physical stimulation on the areola/nipple in a biomechanical fashion to trigger the milk ejection reflex (MER);
3. Maintains baseline vacuum level during the pumping session by controlling the key variables of the active positive and active negative actuation;
4. Creates and maintains a close-to-zero-air environment inside the funnel;
5. Physically keeps the nipple in position throughout the pumping session;
6. Manages and controls not only the maximum vacuum level of a suckling profile programme/cycle but the level of oscillation within a defined vacuum range within a programme/cycle. The active actuation areas of the invention therefore replicate the areas of the infant's tongue that he/she uses more than other areas to achieve the complex suckling mechanism, namely the anterior and the posterior tongue. The breast pump of the invention is configured to actuate and control the active actuation areas independently and in coordination with each other. This allows a variety of programming and control methods. This allows sophisticated and accurate configuration to replicate the complexity of functions of the infant's tongue during suckling. In short, the controlled and separated actuation of the actuation areas' key variables and the order in which these are sequenced in relation to each other therefore allow for the accurate replication of the complex functions of an infant's tongue during suckling.

The lips of the deformable body are optimised for sealing the funnel in place on the breast/areola/nipple in an analogous manner to an infant's lips, and can take a range of shapes including but not limited to cylindrical, oval, parabola shaped, circular or other suitable geometry or the combination of those where sections can extend further than others.

Core suckling profiles such as latch, nutritive suckling (NS) and non-nutritive suckling (NNS) or variations of these can be defined by a predefined pattern of positive and negative actuation of the anterior and posterior actuation areas. Various operational settings defined by the control and sequencing of the key variables such as origin point; displacement distance of the actuation areas along the trajectory of the displacement; displacement direction; angle of displacement measured along the mid-plane of the length of the funnel and measured away from of the mid-plane of the length of the funnel; actuation sequence; acceleration, deceleration and timing of one suckling cycle; frequency, velocity, acceleration, deceleration and timing of one displacement can also be employed. More particularly, the predefined patterns can be defined by the control and sequencing of the key variables selectable from the group comprising or consisting of but not limited to: origin point of the active actuation area; travel distance of the active actuation area along the trajectory of actuation; displacement direction of the active actuation area; angle of displacement of the active actuation area; actuation sequence of the active actuation areas independently and in coordination with each other; frequency, velocity, acceleration, deceleration and timing of each actuation within one suckling cycle; and frequency, velocity, acceleration, deceleration and timing of each cycle within one suckling programme.

BRIEF DESCRIPTION OF THE DRAWINGS

The invention will now be described, by way of example only, with reference to the accompanying drawings in which.

DETAILED DESCRIPTION OF THE INVENTION

Figure 1:
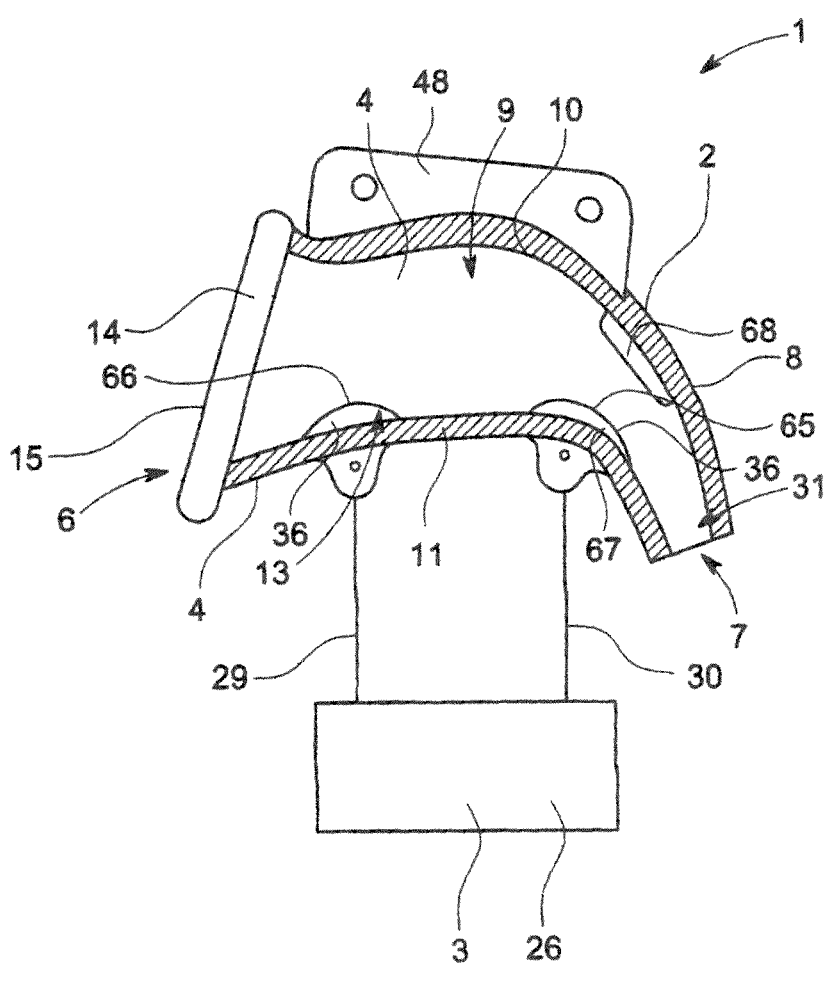
FIG. 1 is a side elevation of a breast pump of the invention made up of a deformable funnel having anterior and posterior active actuation areas and an actuator or actuators (i.e. a driving mechanism) connected to the funnel via drivetrains to biomechanically actuate the actuation areas on the funnel.

As shown in the drawings, a biomechanical breast pump for expressing breastmilk is generally indicated by the reference numeral 1 and is made up of a deformable funnel 2 actuatable by an actuator or actuators 3 (i.e. a driving mechanism) to accurately replicate the complex functions of the infant's tongue during suckling to express breastmilk into the funnel 2.

The funnel 2 has a deformable body 4 shape and is configured to generally define a funnel 2 having a proximal open lip end 6 and an open distal milk discharge end 7. The deformable body 4 is made up of a cylindrical funnel wall 8 extending between the lip end 6 and the discharge end 7. The deformable body 4 can be held in place by an external frame (not shown) attached to a frame mounting 48 on the deformable body 4. In the present embodiment, the funnel 2 is shaped to define an undulating wave or curve indicated by the reference numeral 9.

In the present embodiment, the inner cross section of the funnel 2 is cylindrical in shape. However, in other embodiments, the funnel 2 can have an oval, square, parabola or other suitable geometrical shape and can vary within the funnel 2.

The funnel 2 comprises a nipple chamber 22 extending between the proximal lip end 6 and the distal milk discharge end 7. The nipple chamber 22 further comprises a nipple zone 45 and a downwardly curved pharynx 12. The nipple zone 45 serves to comfortably receive the nipple in use and is located in the nipple chamber 22 between the anterior and posterior actuation areas 23,24. The nipple zone 45 serves as a comfort zone for the nipple. As shall be explained more fully below, the texture of the funnel wall 8 alters with location due to physical anatomical and/or suckling replicators and structural reinforcers which can take the form of extrusions, protrusions, changes in geometry, changes in material thickness or inserts of other materials which can be used to locally alter the funnel to accurately replicate the anatomy of an infant's intraoral cavity and to aid and enhance the complex functions of the suckling mechanism. Externally, the cylindrical funnel wall 8 defines an upper wall 20 and a lower wall 21 contiguous with the upper wall 20 extending for the length of the funnel 2.

Figure 16:
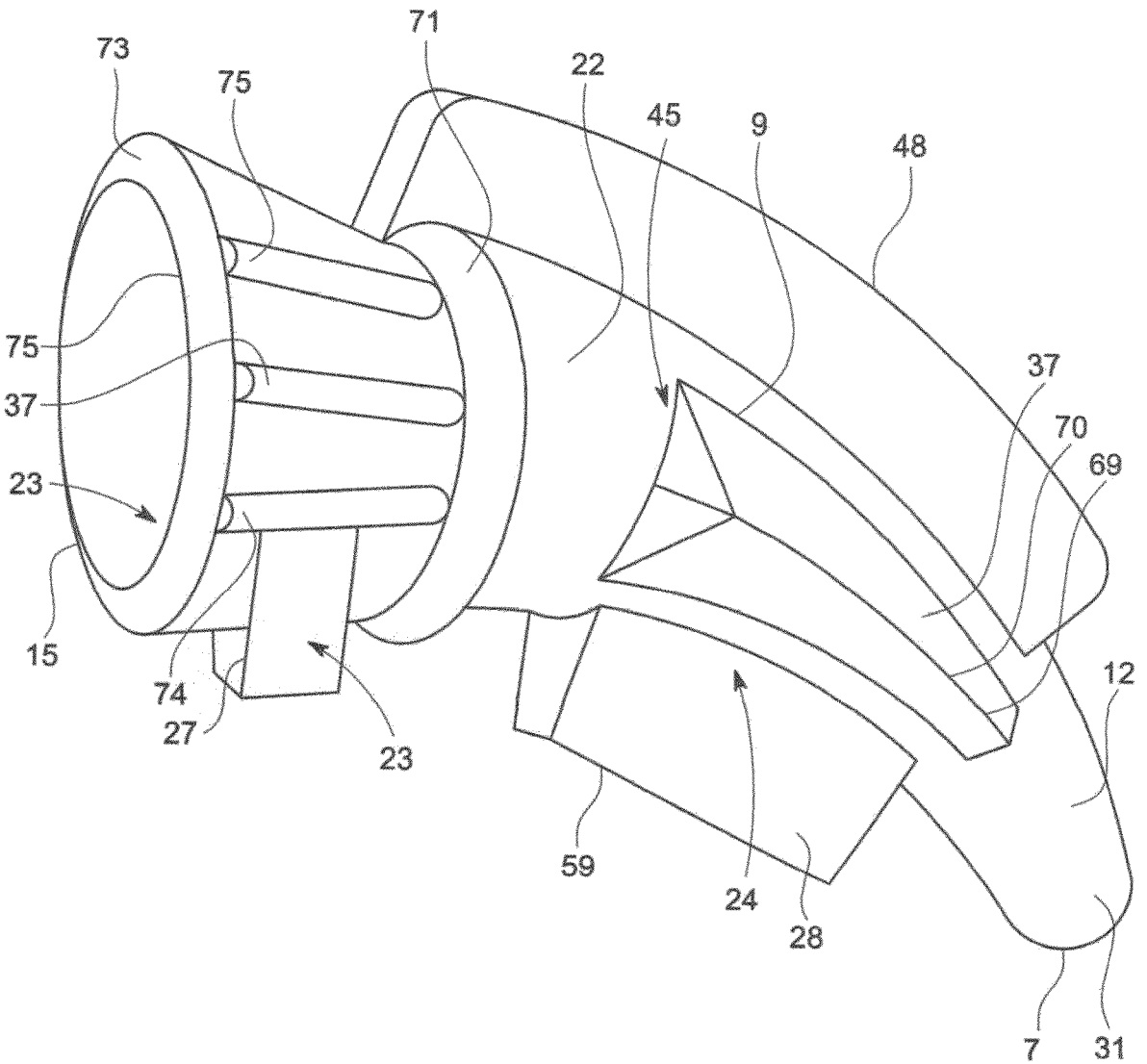
FIG. 16 is a perspective view from above and one side of a further embodiment of the invention in which the breast pump is provided with various anatomical and suckling replicators together with structural side reinforcers and the external funnel side reinforcer is in the closed position.
Figure 17:
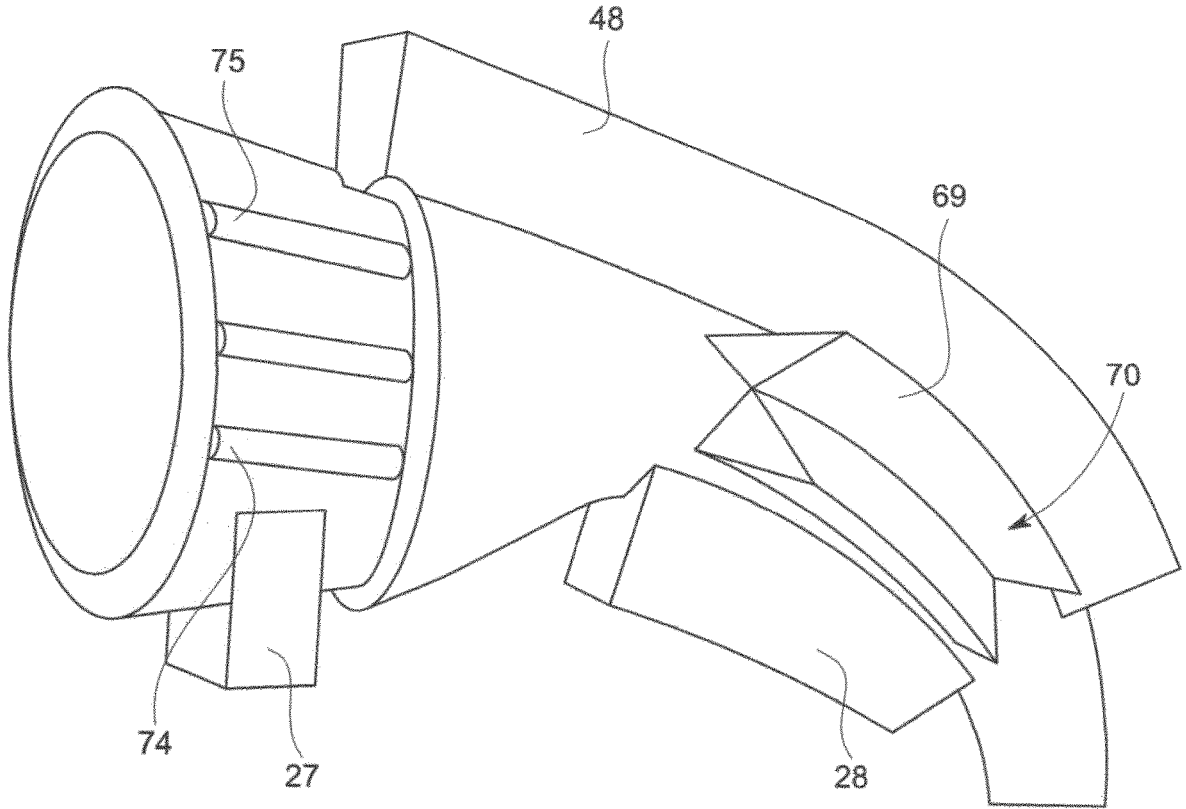
FIG. 17 is a perspective view from above and one side of the breast pump of FIG. 16 with the external funnel reinforcer in the open position.
Figure 18:
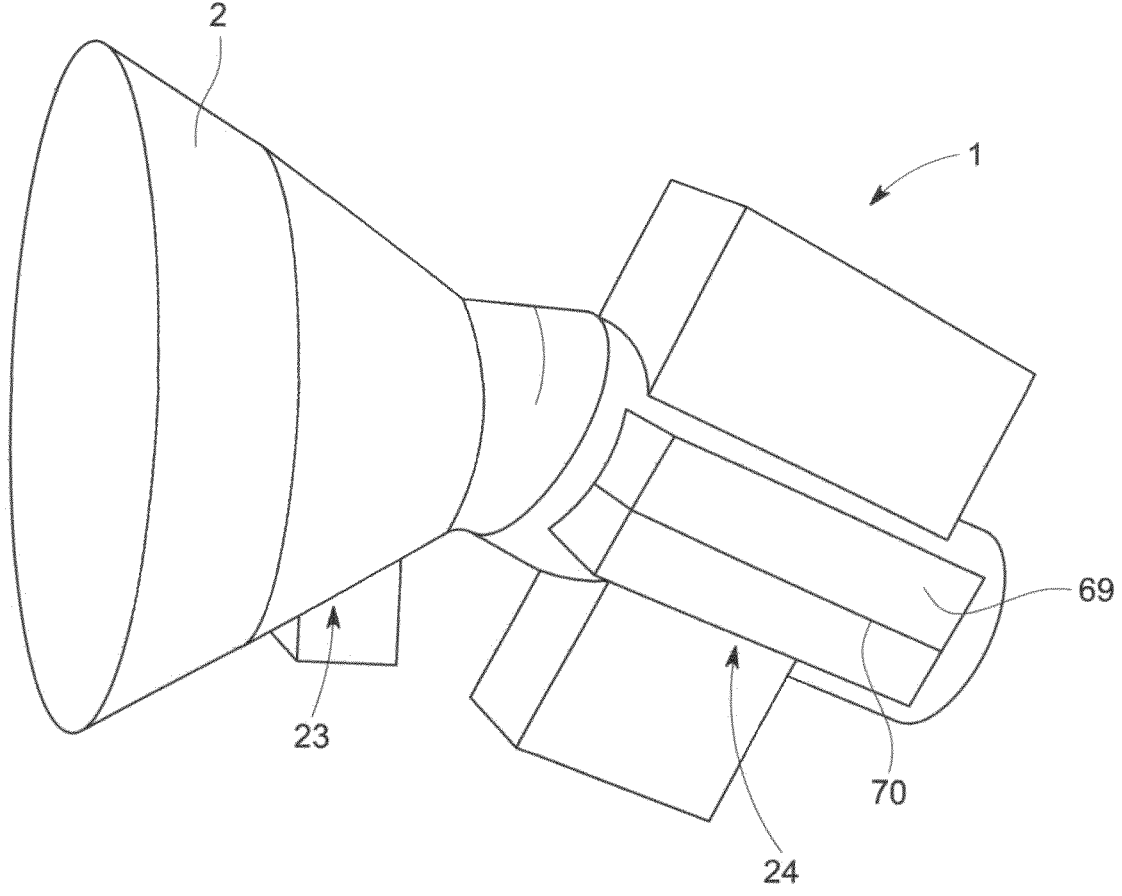
FIG. 18 is a perspective view from above and one side of an alternative embodiment of the breast pump of the invention in which the external structural reinforcer is generally square in cross-section.

The funnel 2 is a flexible structure that replicates the geometry and surface texture of an infant's intraoral cavity and internally, funnel wall 8 is shaped and configured to define an upper relatively hard palate 10 at the upper wall 20, an oppositely disposed lower soft floor 11 at the lower wall 21 opposite the upper hard palate 10, the nipple zone 45, the downwardly curved pharynx 12 which channels the milk towards a discharge outlet 19 defined at the distal milk discharge end 7, the tongue 13 at the lower soft floor 11 and circular lips 14, made up of a bottom lip portion 14a and a contiguous upper lip portion 14b, defining a nipple mouth 15 at the proximal open lip end 6. As shown in FIGS. 16 to 18 described in more detail below, in other embodiments, the lips 14 can be shaped as required e.g. can be elliptical, parabolic or some other geometric profile or profiles to receive a nipple 16 and areola 17 of a user in use.

Figure 7:
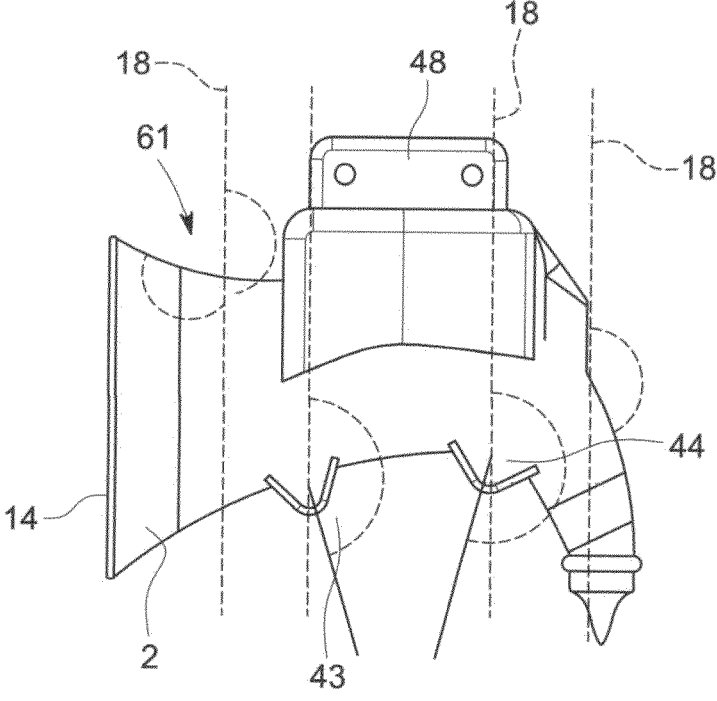
FIG. 7 is a side elevation of the funnel of FIG. 1 indicating anterior and posterior actuation area controllable movement angles.
Figure 8:
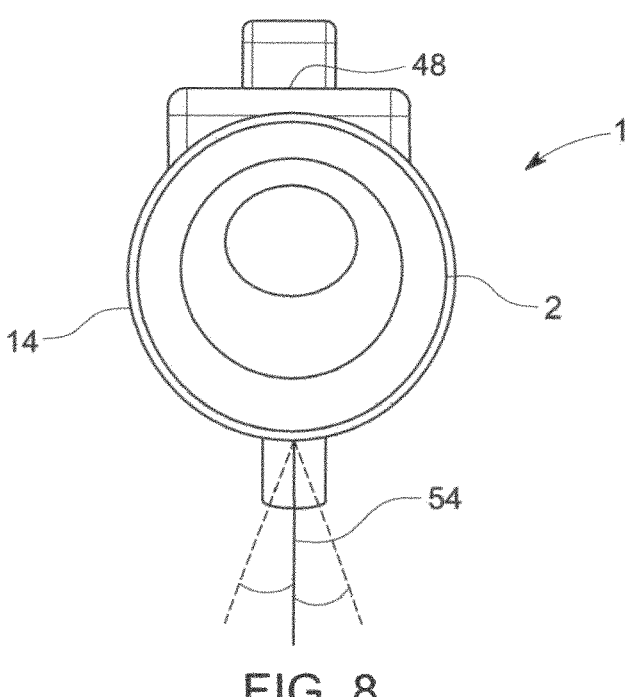
FIG. 8 is a front elevation of the funnel of FIG. 1 indicating lateral or mid-plane actuation angles of the anterior and posterior actuation areas.

As indicated above, in present embodiment the pharynx 12 is adapted to curve downwards at an angle in the funnel 2. The angle of this curve can vary from 90 to 240 degrees. The angle of the pharynx 12 is measured from north (i.e. a vertical axis) in a clockwise direction, where north is a vertical axis indicated by the reference numeral 18 (see FIG. 7). In the present embodiment, the vertical axis 18 is parallel to a vertical line of the frame mounting 48 of the current embodiment. Other embodiments may define this north as any equivalent line which is parallel to this currently defined embodiment.

The funnel wall 8 of the deformable funnel 2 is provided with defined anterior and posterior active actuation areas 23,24 independently, separately and simultaneously actuatable by the actuators 3 (discussed further below) to manipulate the funnel 2 in use to replicate the complex functions of an infant's tongue during suckling in a biomechanical fashion. More particularly, the lower wall 21, is provided with an independently, separately and simultaneously anterior active actuation area 23 disposed towards the proximal lip end 6 and a spaced apart independently, separately and simultaneously posterior active actuation area 24 disposed between the anterior actuation area 23 and the distal milk discharge end 7. The anterior actuation area 23 and the posterior actuation area 24 are located on the lower wall 21 at the lower soft floor 11.

In other embodiments of the invention, the funnel 2 can be provided with additional active actuation areas to aid or enhance the complex functions of the suckling mechanism e.g. sub-atmospheric pressure generation, increase the peristaltic motion of the deformable body in use and further stimulate the areola/base of the nipple, possibly fulfilling other functions too. Examples of such additional active actuation areas include lateral actuation areas which can also have external actuation bodies and can perform similar functions to the anatomical and/or suckling replicators and structural reinforcements if desired.

The upper hard palate 10 defined in the upper wall 20 functionally replicates an infant's hard palate and is co-operable with the active actuation areas 23, 24. The upper hard palate 10 is maintained in a non-moving or stationary position by the breast pump. The upper hard palate defines a passive or stationary actuation area 25 which extends along the upper wall 20 for a distance commensurate with the distance between the opposite anterior active actuation area 23 and the posterior active actuation area 24. The opposing active actuation areas 23, 24 are therefore actuatable against the stationary actuation area 25. This shall be explained more fully below.

The area of the nipple chamber 22 above the lower wall 21 between the anterior and posterior actuation area 23,24 defines the nipple zone 45 (see FIG. 12) which includes a section of the nipple chamber 22 and the pharynx 12. The nipple zone 45 is the area where a nipple 16 is approximately positioned during milk extraction.

Figure 11:
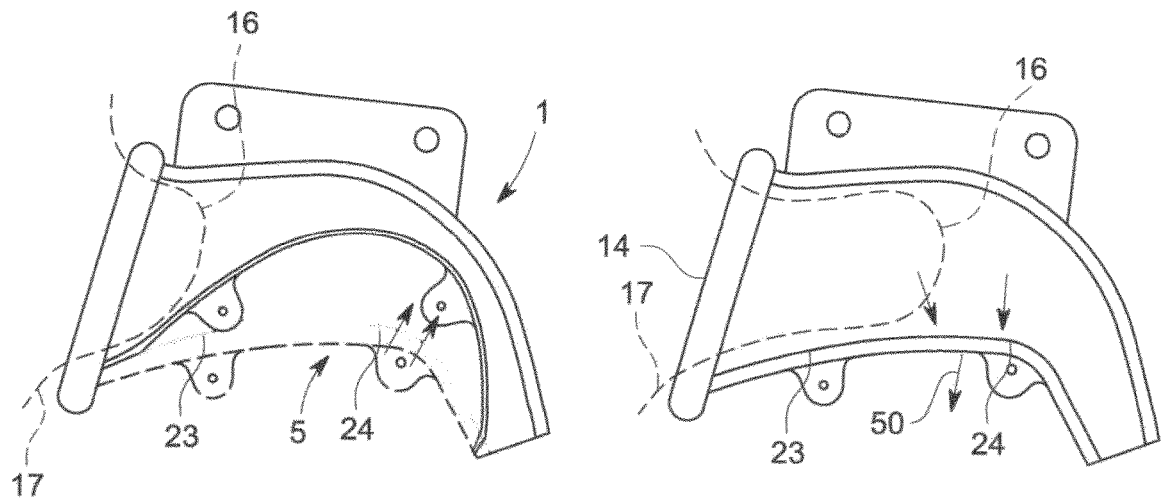
FIG. 11 is a side elevation of the breast pump of FIG. 1 illustrating a latch mechanism achieved by complete positive actuation of the posterior actuation area followed by negative actuation, which generates vacuum within the funnel and air-seal on the areola/breast simultaneously.
Figure 12:
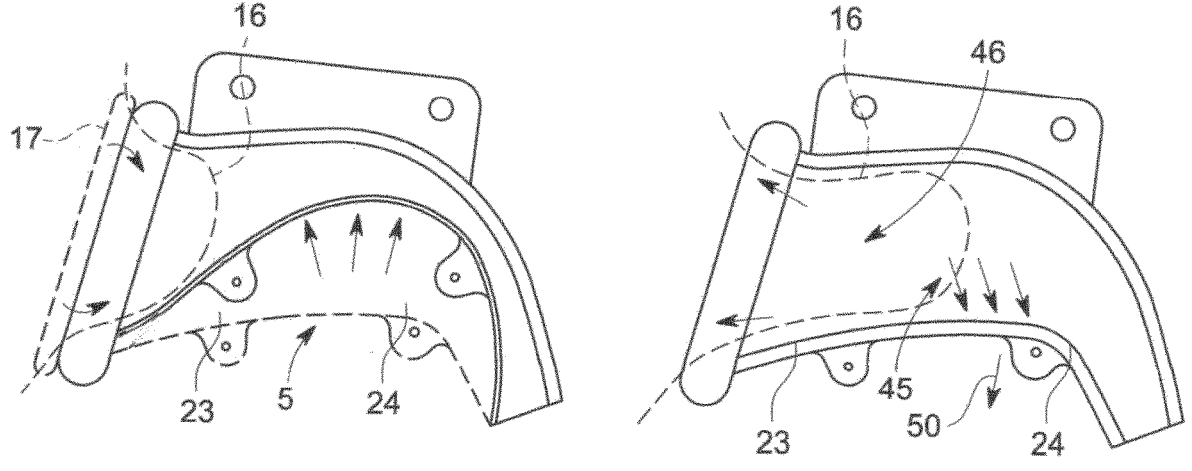
FIG. 12 is a side elevation of the breast pump mechanism of FIG. 1 illustrating an alternative latch mechanism achieved by compressing the middle part of the funnel and rolling back the lips of the funnel followed by releasing both forces to generate a vacuum within the funnel.
Figure 13:
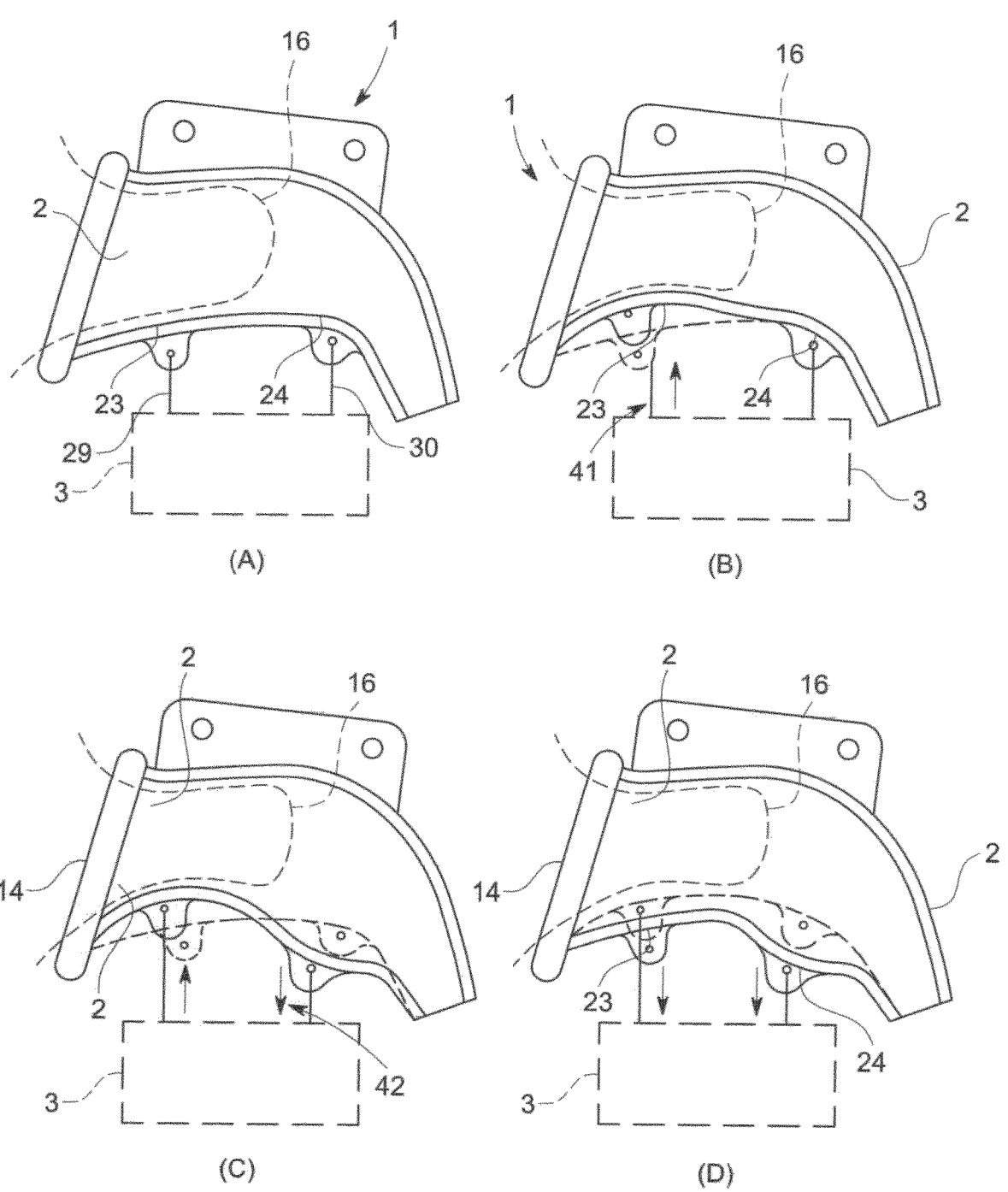
FIGS. 13(a) to 13(d) illustrate one possible sequential positive and negative actuation of the anterior and posterior actuation areas of the funnel.
Figure 14:
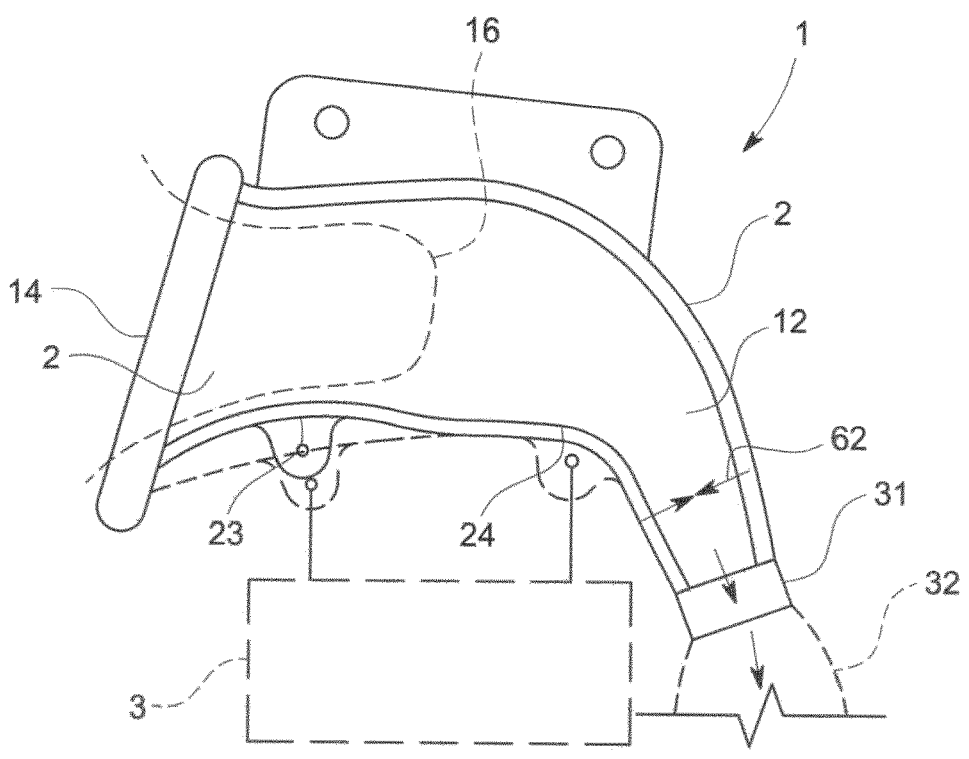
FIG. 14 is a side elevation of the breast pump of FIG. 1 with expressed milk being discharged through the one-way valve of the milk discharge end via a closure point.

One of the functions of the anterior actuation area 23 is the stimulation of the areola 17/nipple 16 as indicated by the reference numeral 41 in FIGS. 11 and 12. The area above the anterior actuation area 23 comprises a stimulation zone 46 (see FIG. 12). The anterior actuation area 23 applies a rhythmical physical stimulation on the areola 17/nipple 16 with each cycle. This locomotion of the actuation area 23 of the funnel 2 is biomechanically similar to that of the physical stimulation of an infant's tongue. The anterior actuation area 23 also contributes to the management and control of sub-atmospheric pressure levels.

The actuator 3 is connected to anterior and posterior drivetrains 29,30 via anterior and posterior actuation bodies 27, 28 disposed on the outer face of the funnel wall 8 corresponding with the anterior and posterior active actuation areas 23,24 respectively which in the embodiment described in FIGS. 1 to 15 are in the form of anterior and posterior drive mountings 27,28. The anterior and posterior actuation bodies 27,28 can be interior or exterior actuation bodies 27,28. In the present embodiment, the anterior and posterior actuation bodies 27,28 are external anterior and posterior actuation bodies 27,28. The anterior and posterior actuation areas 23, 24 are therefore actuatable by the actuator or actuators 3 which can be any suitable drive 26 that can be connected directly or in translation by the drivetrain 29,30 to the funnel and function as a minimum two-way actuator 3 e.g. in the present embodiment the actuator 3 can be an electromechanical motor, servo motor, stepper motor, piston, lever arm, electromagnets, linear driver, solenoids, gears, pneumatic, hydraulic drives or other motors. In short, the electromechanical or mechanical drive 26 is connected to the lower wall 21 at the anterior and posterior drive mountings 27,28.

In other embodiments of the invention, the drivetrains 29,30 can be omitted and the actuator(s) can be connected directly to the actuation bodies 27,28.

The active anterior and posterior actuation areas 23, 24 and the stationary actuation areas 25 can be embedded in lower wall 21 and the upper wall 20 respectively through molding, overmolding, gluing, embedding a harder material in the funnel wall 8 (e.g. inserts) or in other ways familiar to those skilled in the art. In other embodiments, the drive mountings 27,28 as with the actuation areas 23,24 and 25 can be formed by inserts in the funnel wall 8, or as thickening of the funnel wall 8 to achieve the desired rigidity.

The actuation areas 23,24,25 are sized, shaped and placed relative to the shape, size and material choice of the funnel 2.

A one-way valve 31 allows fluid to exit the funnel 2 but prevents air or fluid from returning into the funnel 2. As shown in FIG. 9, the one-way valve 31 is provided adjacent the distal milk discharge end 7 of the funnel 2. The one-way valve 31 can be integrated with the funnel 2 as shown in the drawing for discharging expressed milk into a milk container 32 provided with a milk inlet 34. In another embodiment, the one-way valve 31 can be attachable to and detachable from the funnel or integrated into the milk container 32 and can be attachable to and detachable from either unit.

Figure 10:
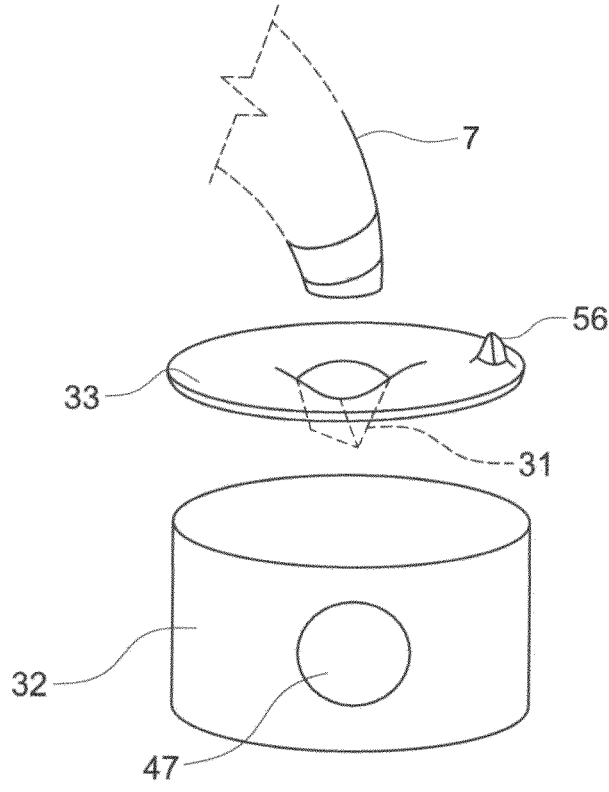
FIG. 10 is a perspective view from above and one side of an alternative outlet one-way valve in which the outlet one-way valve is on a membrane also provided with a one-way air valve.

As shown in FIG. 10, in an alternative embodiment, the one-way valve 31 can be located on a separate membrane 33 attachable to and detachable from the distal discharge end 7 of the funnel 2 as well as the milk container 32.

The design of the one-way valve 31 is defined by the shape, width and thickness in material and its dimensions can be varied as required e.g. in accordance with material choice of the valve as well as the shape and dimensions of the milk container 32 opening (not shown).

In one embodiment, the milk container 32 can also be provided with a one-way air valve 56 to release excess air build-up as the container gradually fills with fluid. The one-way air valve can be part of the milk container 32 or, as shown, the air valve 56 can be incorporated into the membrane 33.

The milk container 32 can be in the form of a bottle or storage bag formed from a variety of materials including, but not limited to, plastics and rubbers.

In another embodiment, the breastmilk pump 1 of the invention can incorporate an auxiliary fluid expulsion enhancement mechanism in the form of a pressurised milk container 32 described above. The pressurised milk container 32 is connectable to the one-way valve 31 as described above and can be primed with a negative pressure to introduce a minimal suction force on the funnel 2 to enhance milk expulsion. This suction force can also optimise and prime the breast pump 1 for an initial latch (discussed further below). This can be executed by compressing the pressurised milk container 32 or a flexible pressurising membrane 47 (e.g. a side membrane 47) on the pressurised milk container 32 that can be compressed to expel air from the pressurised milk container 32 before attempting to return to its original shape upon release indicated by the reference numeral 50 (see FIGS. 11 and 12).

The pressurised milk container 32 can be attached to the one-way valve 31 of the funnel 2, or the membrane 33 by any suitable means such as but not limited to a threaded fitting or an o-ring or by simply pressing the parts together.

The inner geometry and in particular the inner diameters of the cylindrical funnel 2 can be varied to accommodate a variety of breast and nipple sizes to further enhance functionality. Lip length is generally between 10 mm and 70 mm, the angle of the lips 14, indicated by the reference numeral 61, is generally between 270 and 360 degrees for the top lip portion 14*b* and between 180 and 270 degrees for the bottom lip portion 14*a*, but can be different from these figures. (As previously, the angle of the lips 14 is measured from the vertical axis 18/north in a clockwise direction). The inner length of the funnel 2 is generally between about 30 to about 150 mm, the inner diameter generally varies between about 5 mm and about 60 mm, pharynx 12 length is generally between about 0.5 mm to about 70 mm and pharynx 12 diameter is generally between about 2 mm and about 40 mm. However, as will be appreciated by those skilled in the art, these dimensions can vary. The inner geometry of the funnel is generally cylindrical, but, as indicated above, can also be parabolic, oval, square or other suitable geometrical form or the combination of these. The outer diameters are dependent on the material choice and whether the actuation areas 23,24,25 are embedded in the funnel wall 8, externally attached or the actuation areas' functionality is simply achieved by increasing the thickness of the funnel wall 8 at the actuation areas 23,24,25 to create external actuation bodies 27,28 (such actuation bodies are discussed further below).

The deformable funnel 2 can be made from any suitable flexible or resilient material silicone, poly elastomer, rubber or similar having a suitable durometer hardness. The durometer hardness is selected to give enough flexibility to allow for manipulation via the actuator or actuators 3 but resilient enough in defined locations to allow the funnel 2 to remain operable as the vacuum pressure builds up inside it. The actuation areas 23,24 and 25 are generally made from materials having a hardness ranging from about ShoreA-20 to about ShoreD-80 while the funnel 2 generally involves a material makeup of about Shore00-10 to about ShoreA-80. The deformable funnel 2 can also comprise a material of single shore hardness. The durometer hardness values and materials can vary however.

In other embodiments, the breast pump 1 of the invention may include a fluid flow sensor, a fluid volume sensor, a motion sensor or a temperature sensor or any other sensor deemed necessary to monitor and control any output or input variables observable in the system. These sensors can provide feedback to a microcontroller to alter actuation key variables (discussed further below) for optimal cycling. The invention can also be further enhanced with sensors installed to collect heat, flow rate, pressure and motion data.

As indicated above, in the present embodiment, the actuator or actuators 3 used to manipulate the funnel 2 can be an electro-mechanical or mechanical actuator 26. In alternative embodiments, this can be a variety of actuators, including but not limited to electromechanical motor, servo motor, stepper motor, piston, lever arm, electromagnets, linear driver, solenoids, gears, coils pneumatic, hydraulic drives, or other state-of-the-art features that can be translated into a minimum two-way displacement type of actuation. In some embodiments the actuators 3 are adjacent and directly attached to the funnel 2 through the drive mountings 27,28 and in alternative embodiments the actuators 3 can be located at a distance from the funnel 2, allowing the transfer of actuation through the drivetrains 29,30.

As indicated above and as shown particularly in FIGS. 1 to 3, 9A and 9B, and 16 to 22, the funnel 2 can comprise various combinations of anatomical and/or suckling replicators 36 and/or structural reinforcers 37 and/or fluid discharge enhancers 65 on the inner and/or external faces of the funnel 2 or in the funnel wall 8 at locations of geometric value to replicate an infant's intraoral cavity and locations of functional importance to aid or enhance the functions of the complex suckling mechanism and to assist in discharge of milk from the breast pump as required. The anatomical and/or suckling replicators 36 and/or structural reinforcers 37 and/or fluid discharge enhancers 65 can locally increase flexibility or increase rigidity or alter the internal or external shape of the funnel at predefined areas. These anatomical and/or suckling replicators 36 and/or structural reinforcers 37 and/or fluid discharge enhancers 65 can take the form of internal or external extrusions, protrusions, changes in geometry, changes in material thickness, affixing different materials together using any state of the art method, or the combination of any of the above. The purpose of the anatomical and/or suckling replicators 36 and/or structural reinforcers 37 and/or fluid discharge enhancers 65 is to aid or enhance the functions of the complex suckling mechanism.

The location, shape and size of anatomical and/or suckling replicators 36 and/or structural reinforcers 37 and/or fluid discharge enhancers 65 can vary among the different embodiments of the funnel 2 and several of these methods can be considered for each anatomical and/or suckling replicators 36 and/or structural reinforcers 37 and/or fluid discharge enhancers 65 within one embodiment as well.

Figure 2:
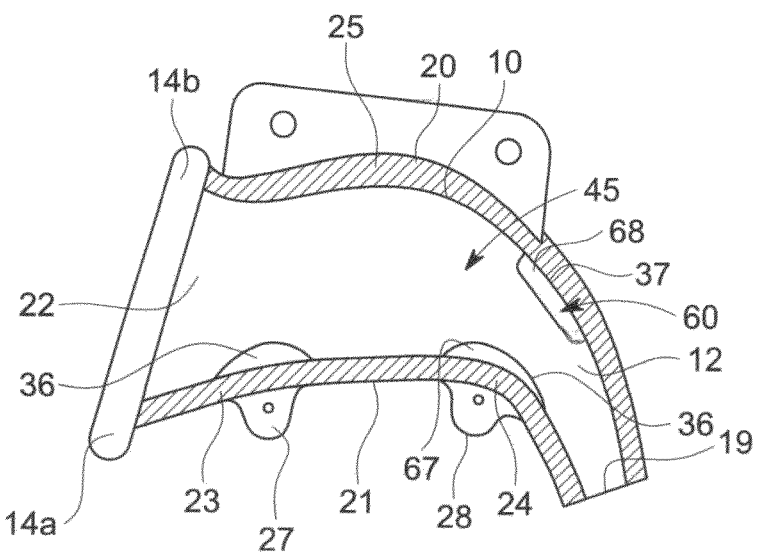
FIG. 2 is a side elevation of the funnel of the breast pump of FIG. 1.
Figure 3:
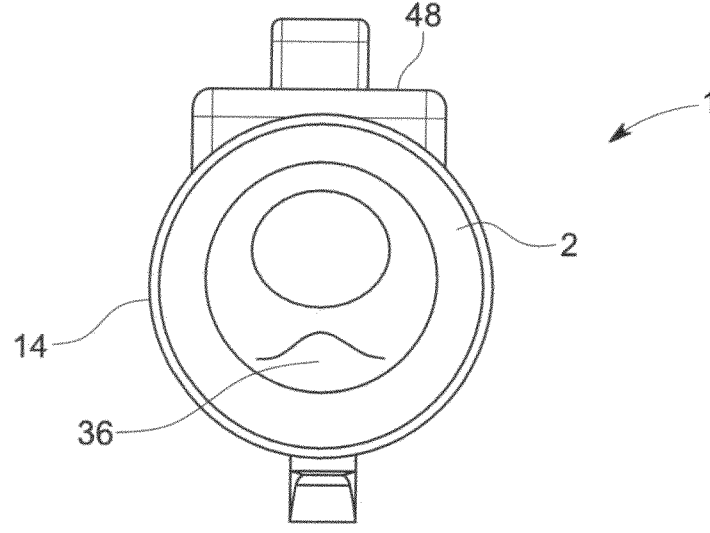
FIG. 3 is a front elevation of an alternative embodiment of the funnel of FIGS. 1 and 2.
Figure 4:
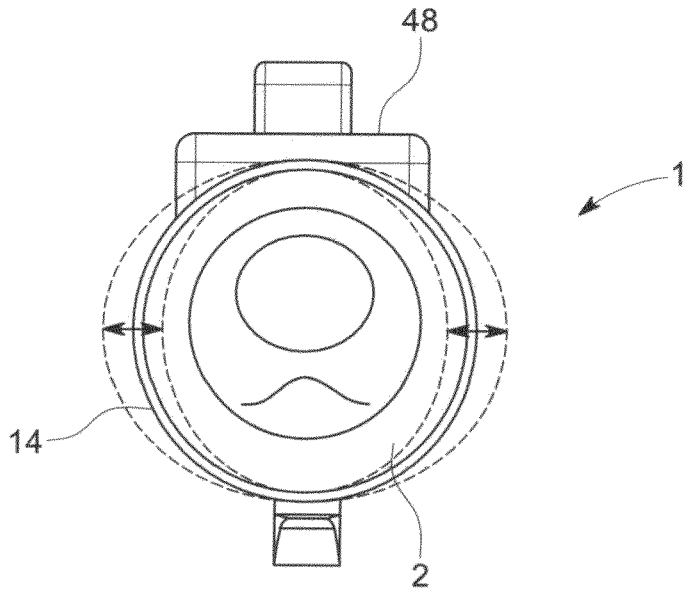
FIG. 4 is a front view of the funnel showing some of the potential shapes of the deformable lips of the funnel of the present embodiment in broken lines.
Figure 5:
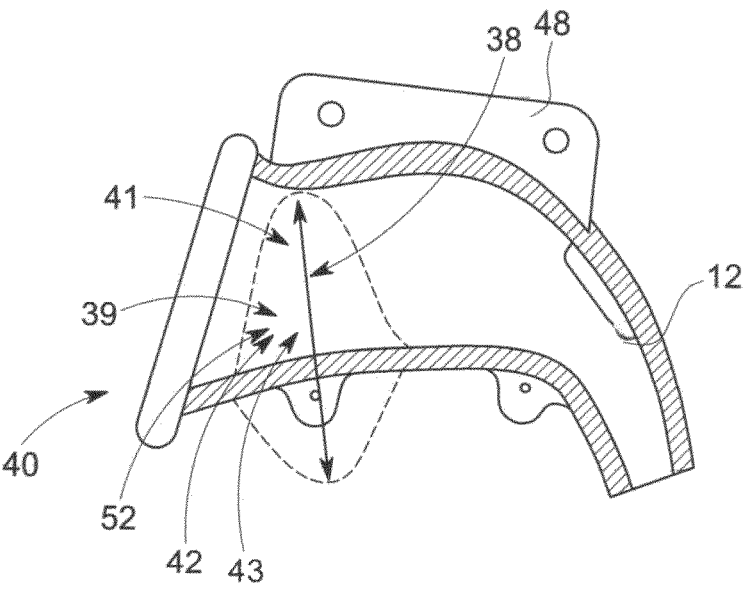
FIG. 5 is a side elevation of the funnel of FIG. 1 indicating the anterior actuation area configuration as controllable values or movements.
Figure 6:
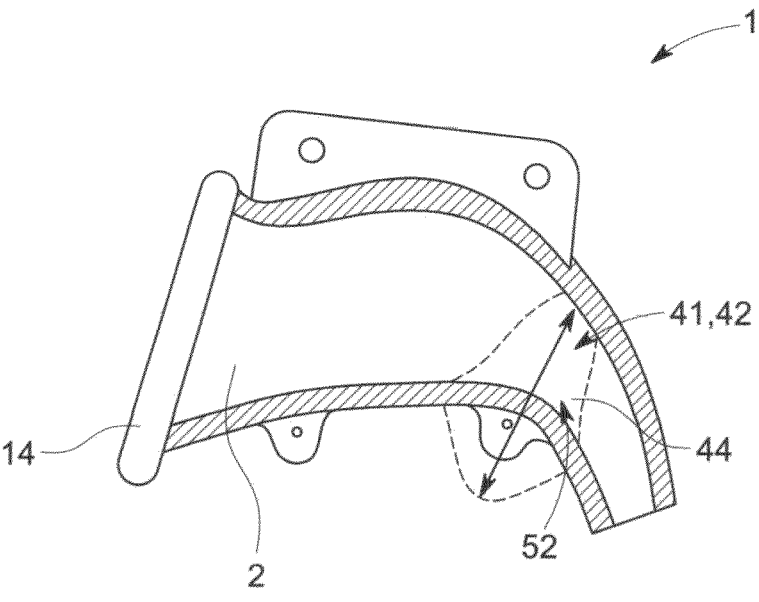
FIG. 6 is a side elevation of the funnel of FIG. 1 indicating the posterior actuation area configuration as controllable values or movements.

As shown in FIGS. 1 to 3, one example of such an anatomical and/or suckling replicator 36 is a nipple base stimulator 66 formed by a bump-like internal protrusion on the internal funnel wall 8 over the anterior actuation area 23 which enhances the stimulation effect on the areola 17/nipple 16. In the present embodiment, the nipple base stimulator 66 takes the form of an internal protrusion in the funnel wall 8. Alternatively, the nipple base stimulator 66 can be formed as a half cylindrical arc shape on the funnel 2 or take several other suitable forms.

Similarly, the breast pump 1 of the present embodiment is provided with an anatomical and/or suckling replicator 36 in the form of a suckling motion and a fluid discharge enhancer 65 in the form of a milk driving replicator 67 on the internal funnel wall 8 over the posterior active actuation area 24. The suckling motion and milk driving replicator 67 is formed as a protrusion which gradually decreases towards the milk discharge end 7.

The funnel wall 8 can also be provided with an anatomical and/or suckling replicator 36 in the form of funnel closing or sealing bodies 68, also in the form of extrusions or protrusions e.g. located on the funnel wall 8 opposite the suckling motion and milk driving replicator 67 to ensure that the distal discharge end 7 is properly sealed at a compression point 60 defined between the suckling motion and milk driving replicator 67 and the funnel closing or sealing body 68 to optimise milk expulsion from the pharynx 12. More particularly, as discussed further below, a cycle can be programmed such that the posterior actuation area 24 presses against the funnel closing or sealing body 68 as required.

In other embodiments, the actuation areas 23,24 can be positioned at other points of interest along the deformable body 4 as required. The compression point 60 also facilitates the sealing of the posterior region to separate the nipple chamber 22 from the pharynx 12 of the deformable body 4 body to enhance fluid extraction.

As indicated above, the anatomical and/or suckling replicators 36 and/or structural reinforcers 37 and/or fluid discharge enhancers 65 can also be located on the external face of the funnel wall 8. Examples of such anatomical and suckling replicators 36 and structural reinforcers 37 are shown in FIGS. 16 to 22. As shown in the drawings, the breast pump 1 of the present embodiment is broadly similar to the breast pump 1 previously described and like numerals indicate like parts.

In the present embodiments, anterior and posterior actuation bodies 27,28 are formed as external structures on the funnel wall 8 to define the anterior and posterior actuation areas 23,24 on the funnel wall 8. More particularly, in the embodiments shown in FIGS. 16 to 21, the external anterior and posterior actuation bodies 27,28 extend the length of the anterior and posterior actuation areas 23,24 respectively on the external face of the funnel wall 8 and can be connected to and activated by the actuators 3 via the drivetrains 29,30.

Externally, the funnel 8 is also provided with various structural reinforcers 37 which prevent elements of the funnel 2 from collapsing under vacuum pressure.

Figure 9A:
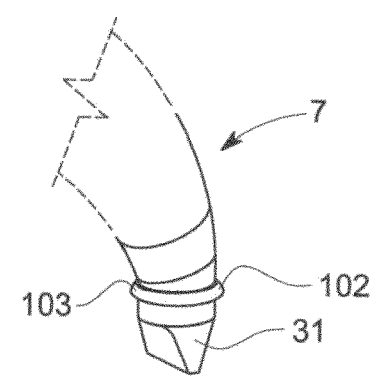
FIG. 9(a) is a perspective view from above and one side of the outlet one-way valve positioned on the pharynx or milk discharge end of the funnel.
Figure 9B:
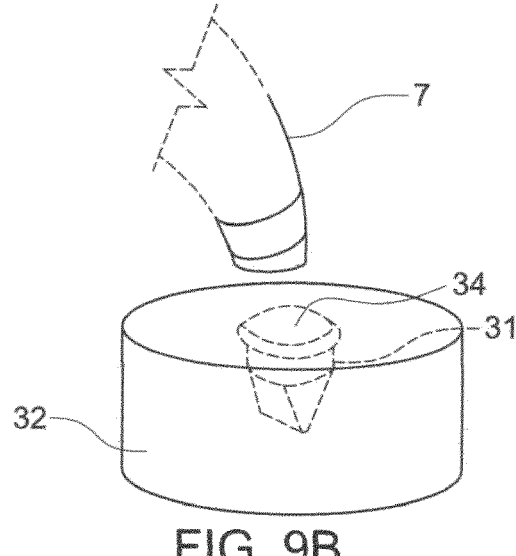
FIG. 9(b) is a perspective view from above and one side of the outlet one-way valve positioned on the breastmilk container.

As shown in FIGS. 9A and 9B, the discharge end 7 of the funnel 2 can be provided with a structural reinforcer 37 in the form of a discharge end reinforcer 102. In the present embodiment, the discharge end reinforcer 102 is provided on the one-way valve 31 in the form of a discharge end reinforcing band 103 at the junction of the one way valve 31 and the discharge end 7.

More particularly, as shown in FIGS. 16 and 17, the funnel wall 8 is provided with a structural reinforcer 37 in the form of an external side reinforcer 69 which extends the length of the posterior actuation area 24 and up to the length of the nipple chamber 22. The elongate side reinforcer 69 has a triangular cross-section and is provided with an inwardly extending openable and closable slit 70 from its apex so that the side reinforcer 69 is movable between a flexed open and a flexed closed position as shown in the drawings. Accordingly, when the posterior external actuation body 28 is moved towards the stationary actuation area 25, the external side reinforcer 69 opens lengthwise along the slit 70 to allow the funnel 2 to be compressed. When the posterior actuation body 28 is moved away from the stationary actuation area 25 the slit 70 closes which reinforces the side of the funnel 2 preventing it from collapsing towards the inside of the funnel 2 as vacuum pressure increases. In this embodiment the entire funnel 2 (including the external side reinforcer 69) is made from a single shore hardness silicone (SA 18) with a funnel wall of thickness of about 1.5 mm.

Moreover, the external anterior and posterior actuation bodies 27,28 can simply be a solid block of the funnel's own material. The anterior and posterior actuation bodies 27,28 provide sufficient reinforcement to ensure that the funnel 2 does not cave in at the active actuation areas 23,24 under high vacuum pressure inside the funnel 2. The anterior and posterior actuation bodies 27,28 can also serve as effective connection surfaces for the drivetrains 29,30 (see FIGS. 20 and 21). The drivetrains 29,30 can be provided with terminal pads 78,79 respectively at their free ends for connecting with the anterior and posterior actuation bodies 27,28. The internal faces of the pads 78,79 can be formed with ridges/ grooves 80 to improve grip with the actuation bodies 27,28. In one embodiment, the pads 78,79 can be formed from a hard plastics or other hard material so that the ridges/ grooves 80 can be pressed into the relatively softer anterior and posterior actuation bodies 27,28 to maintain a firm grip thus preventing the funnel 2 from coming loose in use. The large size and solid nature of the block-like anterior and posterior actuation bodies 27,28 allow the drivetrains 29,30 to affect a secure grip without the risk of losing contact. In addition, due to the substantial nature of the anterior and posterior actuation bodies 27,28 and the amount of material employed in forming the bodies 27,28 the risk of ripping is eliminated as well.

The funnel 2 of the present embodiment is also provided with a nipple chamber reinforcer 71 to reinforce the nipple chamber 22 and particularly the nipple zone 45. The nipple chamber reinforcer 71 is a ring-like protrusion which extends around the funnel 2 at a location in which a nipple is positioned in use to prevent the funnel 2 from collapsing on the nipple during high vacuum pressures in use.

The funnel 2 is also provided with a structural reinforcer 37 in the form of a mouth reinforcer 73 defined about the nipple mouth 15 to also reinforce the funnel 2 to minimise funnel deformation during actuation of the anterior actuation area 23 and to prevent the lips 14 from deforming in use. The mouth reinforcer 73 is also in the form of a protrusion.

Furthermore, the funnel 2 is also provided with a structural reinforcer 37 in the form of lip reinforcers 74 which also prevent funnel deformation at high vacuum pressures. In the present embodiment, the lip reinforcers 74 are made up of lengthwise elongate spaced apart elongate ribs 75 extending between the lips 14, and where present the mouth reinforcer 73, and the nipple zone 22 and specifically the nipple zone reinforcer 72 in the present embodiment.

FIG. 18 shows a perspective view from above and one side of an alternative embodiment of the breast pump of the invention broadly similar to the embodiments previously described but in which the external side reinforcer 69 which extends the length of the posterior actuation area 24 and up to the length of the nipple chamber 22 is generally square in cross-section but is also provided with an inwardly extending openable and closable elongate slit 70 as previously described which is movable between a flexed open and a flexed closed position. It should also be noted that, as with the external side reinforcer of FIGS. 16 and 17, the external side reinforcer 69 can be formed from the same material as the funnel 2 or from a harder shore material in which case the size of the side reinforcer 69 can be reduced.

Figure 19:
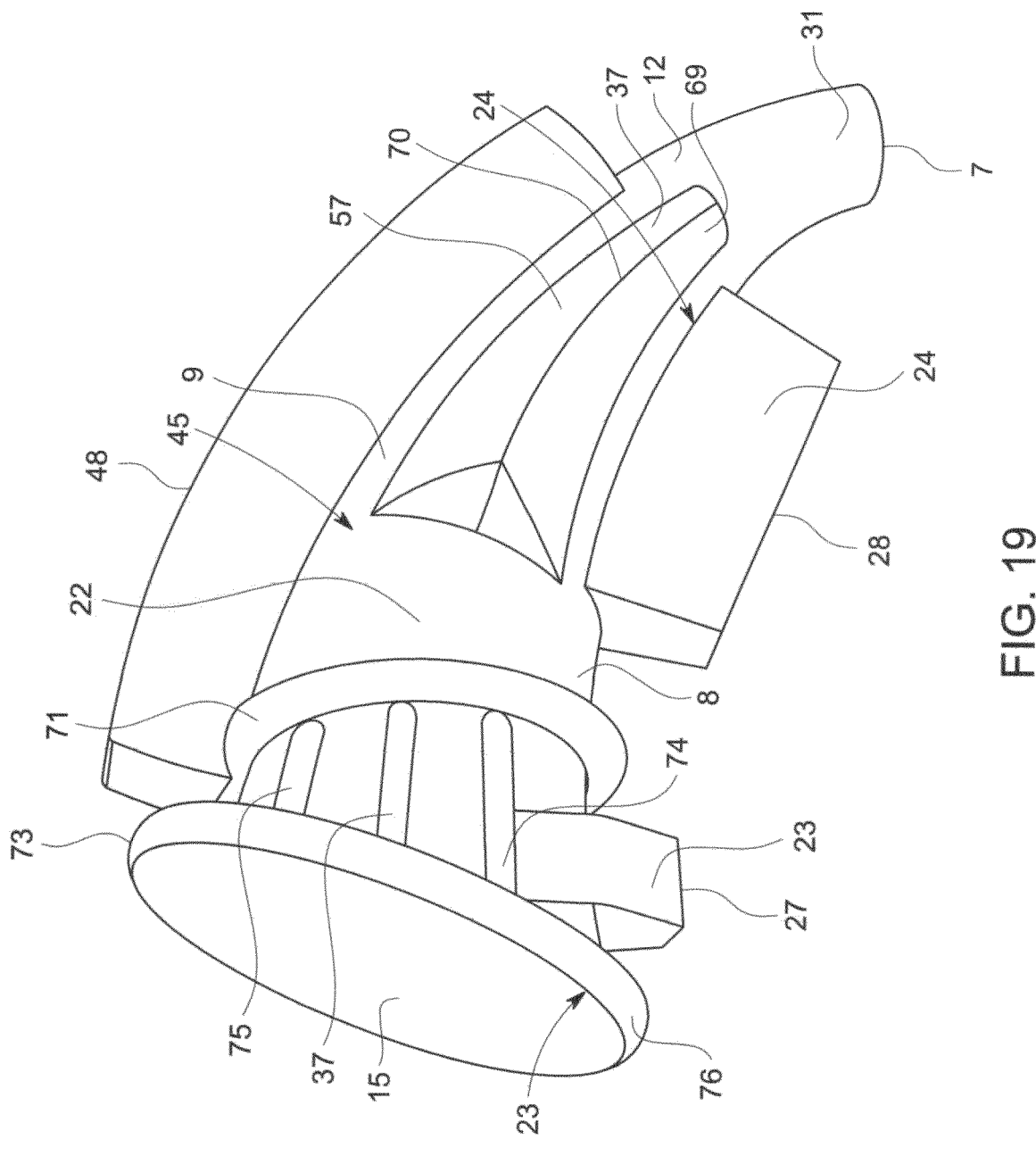
FIG. 19 is a side view of an alternative lip configuration for use in the breast pump of the invention in which a lip is provided with a protruding bottom lip (underbite) portion.
Figure 20:
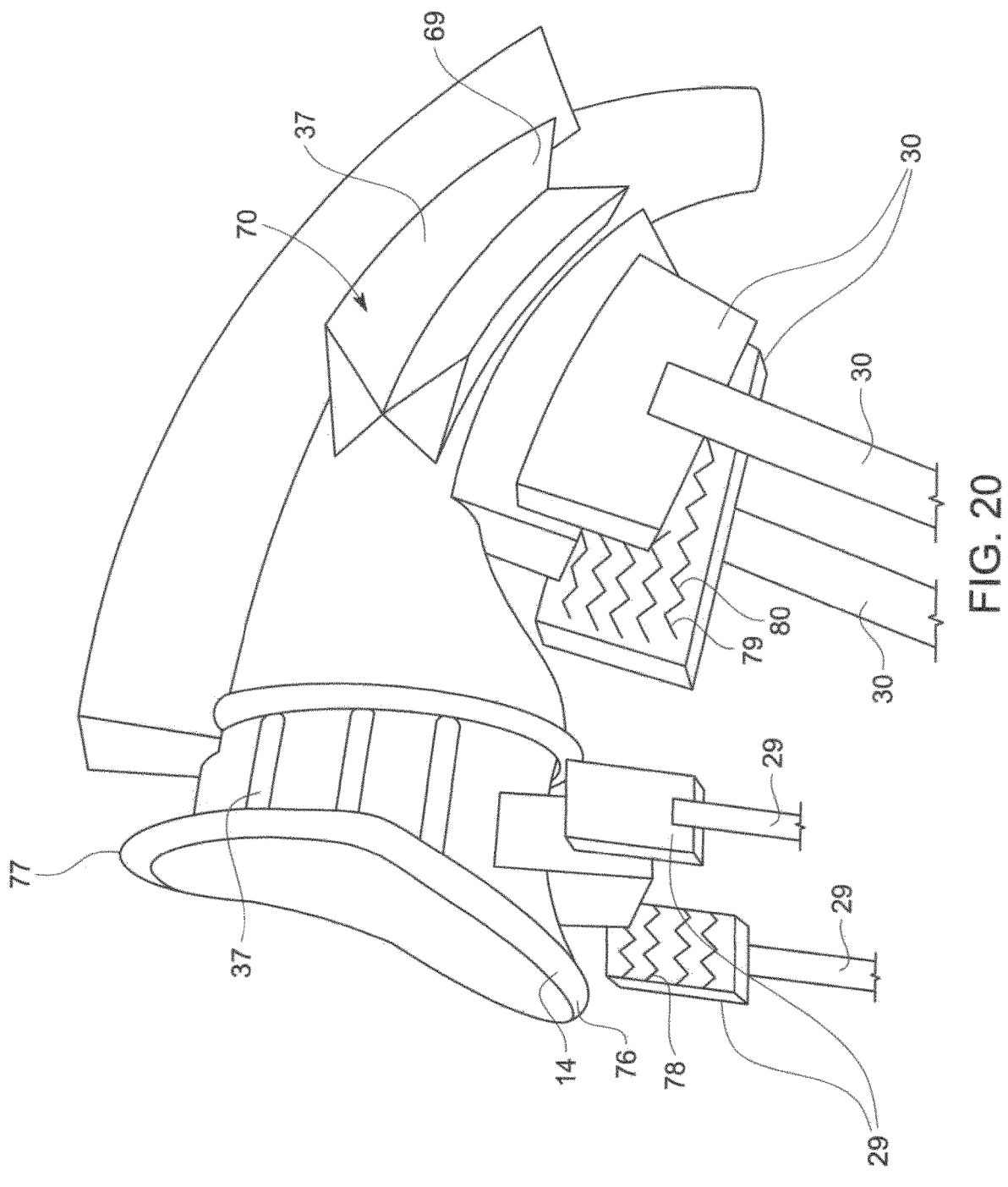
FIG. 20 is a perspective view from below and one side of an alternative embodiment of the breast pump of the invention in which the lips have an alternative biomimetic relatively open V-shape when viewed in profile.
Figure 21:
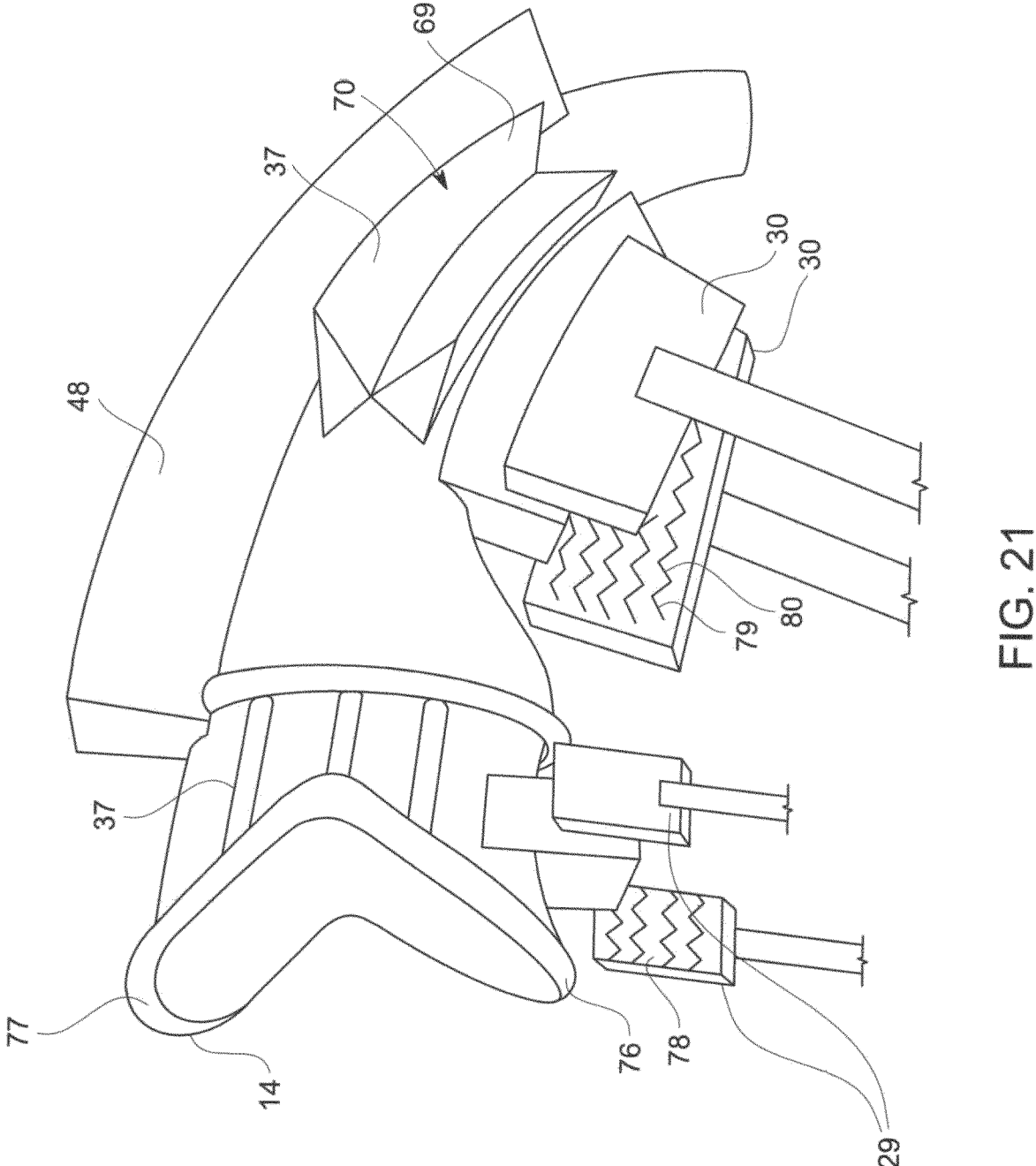
FIG. 21 is a perspective view from below and one side of an alternative embodiment of the breast pump of the invention in which the lips have an alternative biomimetic relatively closed V-shape when viewed in profile.

As shown in FIGS. 19 to 21, the lips 14 of the breast pumps of the invention can also be configured with alternate shapes and configurations to further enhance replication of the suckling effect. For example, as shown in FIG. 19, a lower/bottom lip portion 76 of the lips 14 protrudes from the lips 14 to define an underbite configuration to enhance suckling, in FIG. 20 the lips 14 have a relatively open V-shape when viewed in profile i.e. the lower/bottom lip portion 76 and an upper/top lip portion 77 together define a relatively open or wide V-shape and in FIG. 21 the lower/ bottom lip portion 76 and the upper/top lip portion 77 together define a relatively closed or tight V-shape for enhancing suckling.

In short, the purpose of the aforementioned structural reinforcers 37 is to ensure that the funnel has the right level of flexibility for the actuation and the right level of rigidity to remain operable as the vacuum pressure is building up inside it. The structural reinforcers of the invention ensure that this balance between flexibility and rigidity is achieved.

If desired as indicated above, the breast pumps of the invention can include several other anatomical and/or suckling replicators 36 and/or structural reinforcers 37 and/or fluid discharge enhancers 65 to further aid and enhance the functions of the suckling mechanism.

Figure 22:
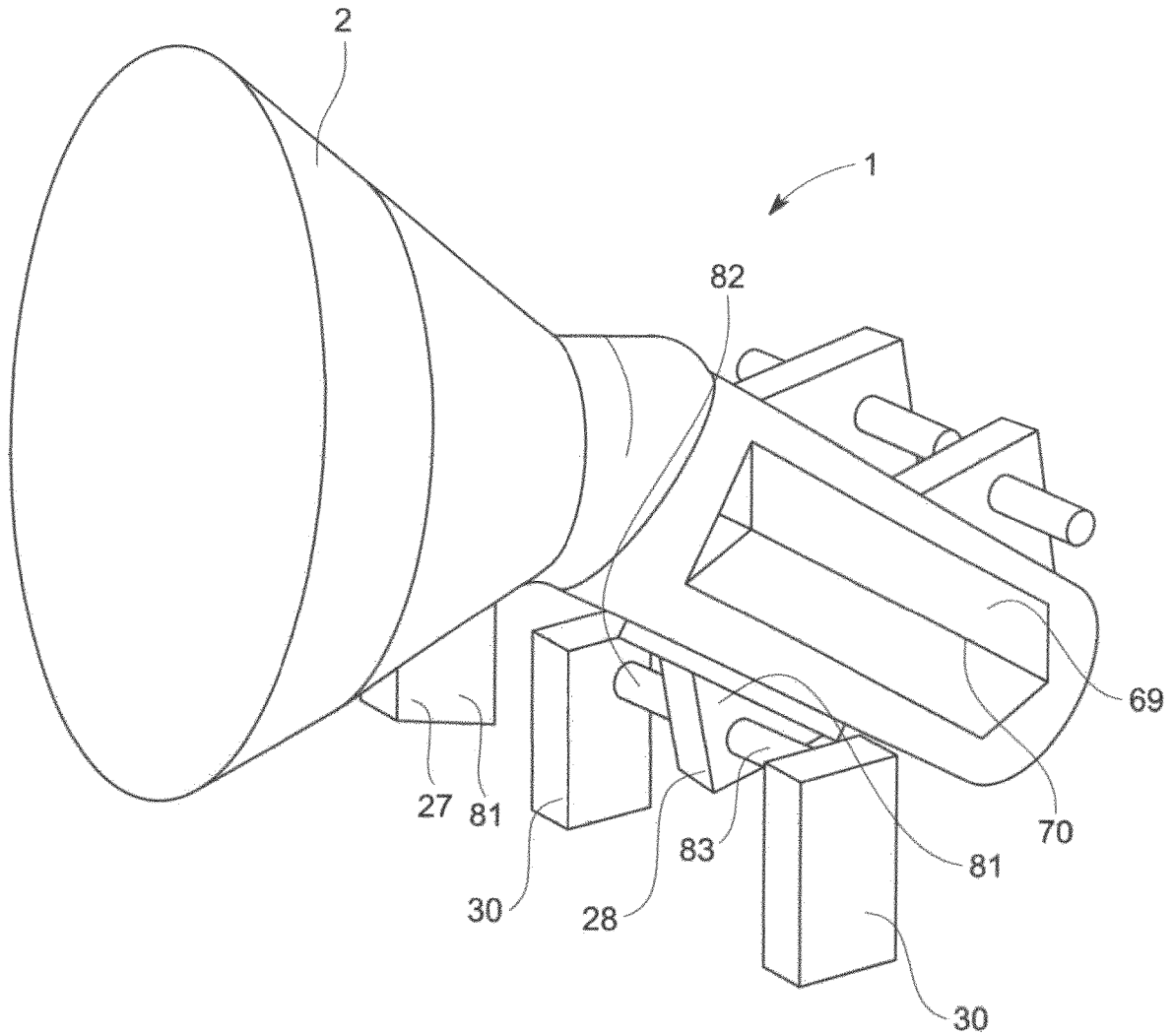
FIG. 22 is a perspective view from above and one side of a breast pump of the invention in which the breast pump is provided with actuation bodies for connection with the drivetrains in the form of inserts or overmoulds of a relatively higher shore hardness materials inserted into the breast pump funnel wall.

FIG. 22 shows a perspective view from above and one side of a breast pump of the invention in which the breast pump 1 is similar to the embodiments previously described and like numerals indicate like parts. However in the present embodiment, the breast pump 1 is provided with external actuation bodies 27,28 for connection with the pair of drive trains 30 in the form of inserts or overmoulds 81 of a relatively higher shore hardness material (e.g. about Shore A 60) firmly inserted into the breast pump funnel wall 8 e.g. using known gluing or overmoulding processes. The drive trains 29,30 can in turn be connected to the inserts or overmoulds 81 via a link pin 82 extending between the drive trains 30 and a link pin opening 83 defined in the inserts or overmoulds 81. In this embodiment, the drive trains 29,30 can be formed from hard plastics materials. Similarly, the hard palate 10/stationary actuation area 25 can be similarly defined by inserts or overmoulds 81.

Figure 23:
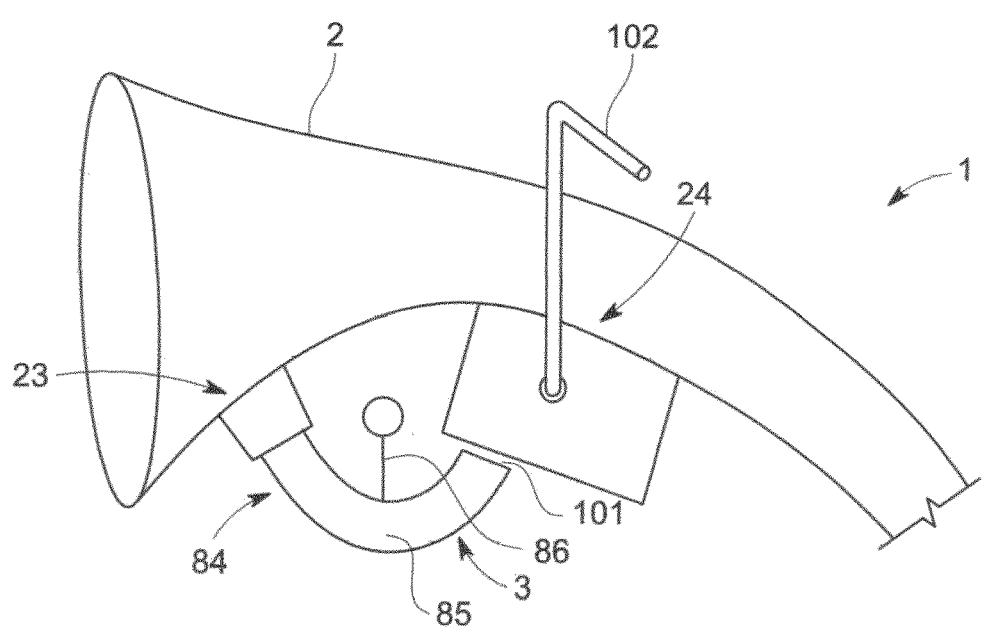
FIG. 23 is a perspective view from one side of a further embodiment of the invention in which the breast pump is a manually operated breast pump i.e. the actuator is a manually operable actuator and the manually operable actuator is in the non-operating position.
Figure 24:
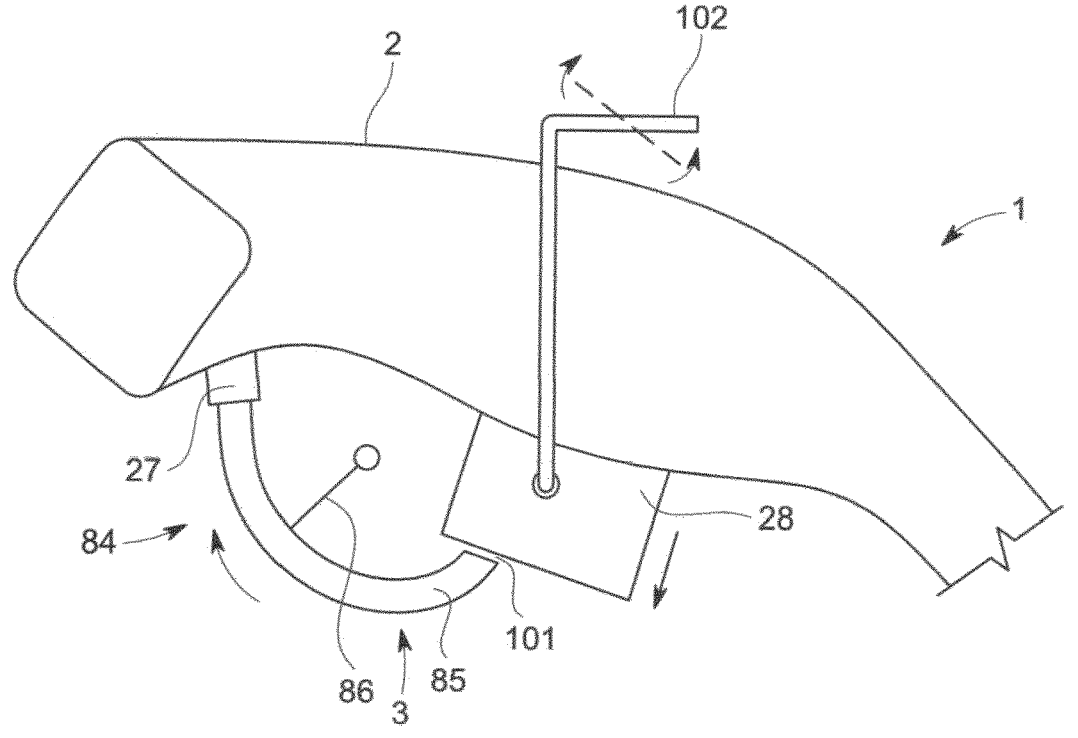
FIG. 24 is a side perspective view of the breast pump of FIG. 23 but with the manually operable actuator in the operating position.

FIGS. 23 and 24 show perspective views from the side of a further embodiment of the invention similar to the embodiments previously described but in which the breast pump 1 is a manually operated breast pump 1 i.e. the actuator 3 is a manually operable actuator 3. Like numerals indicate like parts. As shown in the drawings, the manually operable actuator 3 is a hand controlled drive mechanism 84 made up of an active actuation point connector 85 extending between the anterior active actuation area 23 and the posterior active actuation area. More particularly, the connector 85 is attached at a first end to the first external actuation body 27 and has a second free end disposed adjacent but spaced apart from the second external actuation body 28 to define a gap 101 between the free end of the connector 85 and the second external actuation body 28 so that the first active actuation area 23 can be positively or inwardly displaced independently of the second active actuation area 24 or both active actuation areas 23,24 can be positively displaced simultaneously by urging the free end of the connector 85 against the second active actuation body 28. Similarly, when the posterior actuation body 28 is negatively displaced by a manual lever 102 provided on the funnel wall 8 (i.e. a negative or pulling force in the direction indicated by the arrow in FIG. 24, the anterior actuation area 23 is positively displaced (i.e. a positive or pushing force) in the direction indicate by the arrow about a pivot point 86 defined on the active actuation point connector 85. In the present embodiment, the active actuation connector 85 is substantially semi-circular or crescent shaped. The active actuation point connector 85 can also be provided with a hand grip 87 for ease of use.

In use, the funnel 2 is actuated in positive and negative directions 41,42 at the active actuation areas 23,24. This manipulation is characterised by several variables called "key variables" including:

The origin point 38 is the active anterior and posterior actuation area's 23,24 location on the trajectory of travel at the start of a suckling program or cycle. The origin point 38 is therefore a relative figure that can differ depending on the choice of suckling programme. The origin point's 38 value is 0 (zero) at the closest point the actuation area 23,24 can be in relation to the respective stationary area 25—see FIGS. 5 and 6. The highest value of the origin point is the farthest point the actuation area 23,24 can be from the respective stationary area 25 and so is dependent on the shape and dimension of the funnel 2 and can differ for the anterior and posterior actuation areas 23,24 within one embodiment;

Travel distance 39 as a variable is the length the actuation areas 23,24 can travel in one direction along the trajectory of actuation. The value of the maximum travel distance 39 usually coincides with the distance between the active actuation area 23,24 and it's corresponding stationary area 25 at its most open position and at its widest cross-section see FIGS. 5 and 6. Therefore the value of the maximum travel distance 39 can vary between the different shaped and sized funnel 2 embodiments and it is different for the anterior and for the posterior actuation areas 23, 24. The travel distance 39 varies between programmes and/or cycles, it is independently defined for the actuation areas 23,24, and can be independently defined for the positive actuation 41 and for the negative actuation 42. The travel distance 39 is the main variable for generating and controlling the maximum vacuum level, the baseline vacuum level and the oscillating vacuum ranges. The travel distance 39 as a variable is not the same as the observed travel distance of the actuation areas 23,24 during operation considering the altering effect of the presence of vacuum and fluid dynamics.

Travel direction 40 of the actuation areas 23,24 can be described by 'positive' 41 and 'negative' 42. Positive actuation 41 is defined as the direction when the active actuation area 23,24 is moving or being moved towards the corresponding stationary area 25 and negative actuation 42 is defined as the direction when the actuation area 23,24 is moving or being moved away from the corresponding stationary area 25.—see FIGS. 5 and 6;

Angles of travel 43,44 of the active actuation points 23,24 is measured from the vertical axis 18/north in a clockwise direction. The angle of travel 43 for the anterior actuation area 23 is generally between 100 and 250 degrees, and the angle of travel 44 for the posterior actuation area 24 is generally between 120 and 270 degrees—see FIG. 13. The angle of travel 43,44 can also be defined as the angle away from a vertical mid-plane or axis indicated by the reference numeral 54 defined lengthwise in the funnel 2. Using this alternative definition, the angles of travel 43,44 are generally between 0 to 90 degrees on either side of the mid-plane/axis 54;

Actuation sequence of a suckling cycle is a set of positive and negative actuations 41,42 on both active actuation areas 23,24 defined independently along the key variables which is repeated as required (see below);

Frequency, velocity, acceleration, deceleration, and timing of a single actuation (indicated by the reference numeral 52) within one suckling cycle (see below);

Frequency, velocity, acceleration, deceleration, and timing of one suckling cycle within a suckling profile programme.

As indicated above, actuation is executed by an actuator or actuators 3. Actuation is transferred from the actuator 3 to the funnel 2 through the anterior and posterior drivetrains 29,30 attached to the funnel 2 at the external drive mountings 27,28.

Accordingly, a suckling cycle or programme is transferred through and induced upon the funnel 2 by the anterior and posterior drivetrains 29,30. The length of the anterior and posterior drivetrains 29,30 can vary to serve different purpose. If the drivetrains 29,30 are short, or the drive mountings 27,28 of the funnel 2 are attached directly to the actuator 3 the system is more suitable for a personal use breast pump model. If the drivetrains 29,30 are long it allows the actuator 3 to be at a distance from the funnel 2 allowing the design of a multiple-user model.

In alternative embodiments, it is possible to actuate the active actuation areas 23,24 simultaneously using a single actuator 3 and a single drivetrain 29,30 connecting to both external drive mountings 27,28.

Figure 15:
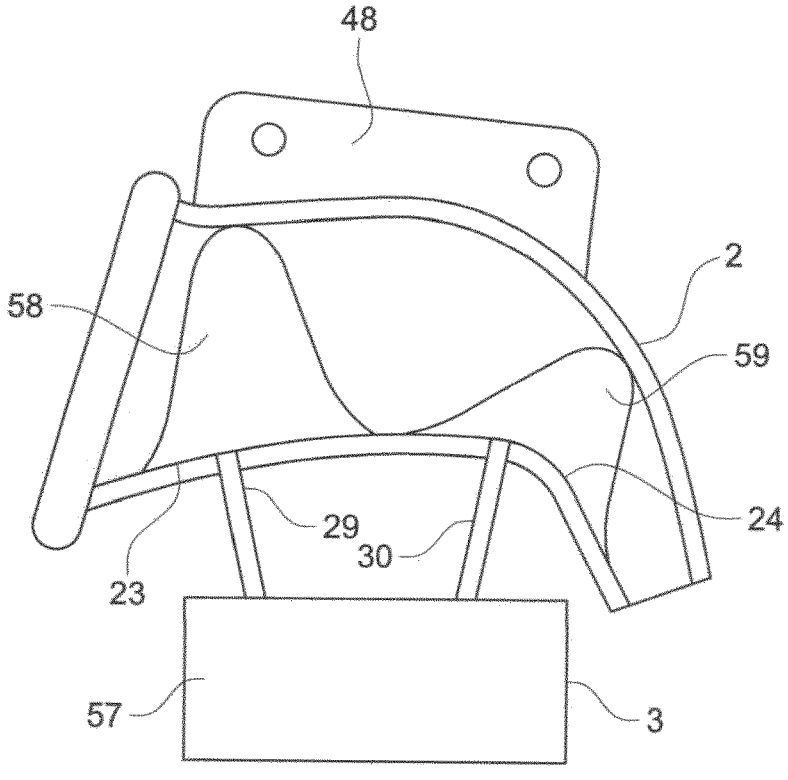
FIG. 15 is a front view of an alternative embodiment of the invention in which the actuator or actuators are a hydraulic or pneumatic pump and the active anterior and posterior actuation areas are provided with internal inflatable and deflatable pouches to create biomechanical movement of the funnel.

As indicated above, the actuator or actuators 3 are equipped with a drive 26 that's capable of, directly or in translation via the drivetrain 29,30, exerting a minimum two-way actuation e.g. is electromechanical motor, servo motor, stepper motor, piston, lever arm, electromagnets, linear driver, solenoids, gears, pneumatic, hydraulic drives (see FIG. 15 where like numerals indicate like parts) or other actuator types. However, other actuator types can be employed such as rotary electrical motors, servomotors, other electromechanical systems or hydraulic/pneumatic actuators as shown in FIG. 15 that can induce 5 locomotion through a reciprocating linear motion for instrokes and outstrokes. Like numerals indicate like parts. As shown in the drawing, in this embodiment, the actuator or actuators 3 is a hydraulic or pneumatic pump 57 in fluid/air communication with the anterior and posterior actuation points 23,24 via the anterior and posterior drivetrains 29,30. In addition, internally, the active anterior and posterior actuation points 23,24 are provided with internal inflatable and deflatable pouches 58,59 respectively to create an internal biomimetic movement of the pouches 58,59. The inflatable and deflatable pouches 58,59 are inflatable and deflatable by the hydraulic or pneumatic pump 57 to mimic the suckling of an infant in the same manner as with the posterior and anterior actuation points 23,24 as 15 defined by the key variables as previously described.

In another embodiment of the invention, the breast pump mechanism 1 can include environmental sensors to monitor variables of interest including, but not limited to, sub-atmospheric pressure within the funnel, compression force within the funnel, fluid flow within the device, volume expressed, temperature of fluid or air, duty cycle of the device, total time of expression. Fluid expression schedule data throughout each 24 hour period can also be recorded in memory if required. This data can be used to automate changes in suckling programmes and/or cycles to optimize efficiency for each user. In addition, the data will allow multiple transitions between nutritive and non-nutritive suckling or other programmes during an expression session.

The level of control and the range of functions of the invention accommodates the system to be programmed to actuate the active actuation areas 23,24 in a wide range of suckling patterns including replicate three distinguishable suckling profiles associated with infant suckling including: the latch, non-nutritive suckling (NNS) and nutritive suckling (NS). Three exemplary core suckling profile programmes are described in detail below. However, as will be appreciated by those skilled in the art, even these sample programmes can be modified further along the key variables to enhance efficacy or to individualize the programmes for users.

Latch

The latch is when the infant takes a nipple 16 into his or her mouth and creates and air-seal around the areola 17 maintaining a baseline vacuum level of approximately 40-70 mm Hg with minimal or no dead-air in the intraoral cavity. To replicate this action, the funnel 2 is initially compressed. This compression is effected manually or by the actuator 3 by pressing the lower wall 21 towards the upper wall 20 at the posterior actuation area 24 or at both actuation areas 23,24.

Alternatively, this initial compression can be achieved in a way that the starting position of the funnel 2 in the breast pump is that the posterior actuation area 24 or both actuation areas 23,24 are in a compressed state.

Alternatively, this result can be also achieved by running a few cycles of other programmes, because by the nature of the invention being a closed air-tight system the first few cycles of positive actuation 41 presses the excess air out through the one-way valve 31 creating and maintaining a close-to-zero-air environment and thus ensuring the nipple 16 to arrive into and stay in position.

Due to the shape and flexibility of the funnel 2, by compressing the posterior actuation area 24 the proximal lip end 6 naturally opens spreading the nipple mouth similarly to an infant's mouth opening as it receives the nipple and areola 16,17 further enhancing the correct positioning of the nipple 16. The proper positioning of the nipple 16 can be further accommodated folding back and releasing the lips 14 and surrounding area.

As the nipple 16 is now in situ, the following negative actuation 42 will allow the lips 14 to return to its original position and the negative actuation 42 will create an adhesion site/seal around the contact area with the breast or areola 17, allowing initial sub-atmospheric pressure formation inside the funnel 2 (the baseline sub-atmospheric pressure). The baseline sub-atmospheric pressure maintains a continuous seal on the breast.

Suckling Profile Programmes

The following characteristics of the breast pump mechanism 1 allows the generation of a wide range of suckling profiles:

Movement of the anterior and posterior actuation areas 23,24 independently but in a coordinated manner in the same direction, or in the opposite direction in sync or in delay to each other;

A suckling cycle is a set of positive and negative actuations 41,42 on both active actuation areas 23,24 defined independently along the key variables and repeated as required;

Programme is a set of the same suckling cycles or a set of different suckling cycles sequenced after one another The actuation 41,42 is on an approximately linear trajectory, however, the actual path of travel can vary due to the restrictive/deformable nature of the funnel 2;

The extent to which each active actuation area 23,24 can positively travel is limited by the funnel wall 8 at its most open position;

The suckling cycle initiated at the anterior actuation point 23. After a short 10 delay, the posterior actuation point 24 follows in the same direction. This delay is less than or equal to the time taken for the anterior actuation point 23 to reach its turning point before returning to the starting position, even if the posterior actuation point 24 has longer distance 39 to travel. This delay, the matching direction of displacement and sequencing of timing achieves the desired wave-like motion;

Negative actuation 42 is generally followed by positive actuation 41. Alternatively, positive actuation 41 is generally followed by negative actuation 42, however this is not always the case;

All key variables can be individually programmed and can be modified to replicate various suckling profiles or serve other purposes;

Sub-atmospheric pressure is mainly generated by the posterior actuation area 24. When the nipple 16 is in position in the nipple zone 4 and a negative actuation 42 is performed at the posterior actuation area 24, it increases the volume of space inside the funnel 2 during the volume of air remains the same because the system is air-tight. This increase in volume generates increase of the vacuum level inside the funnel 2. The vacuum suction draws the milk from the breast into the funnel 2.

In general, an increase in magnitude of negative actuation 42 on the posterior actuation area 24 results in an increase in vacuum level. Thus, reducing the vacuum level inside the funnel 2 is simply done by positive actuation 41 of the posterior actuation area 24. The actuation of the anterior actuation area 23 can aid to further increase the vacuum level (negative actuation) or decrease the vacuum level (positive actuation) for a more accurate control.

The positive actuation 41 of the actuation areas 23,24 is controlled in a manner to ensure that the travel distance 39 is not too long to compromise the baseline sub-atmospheric pressure level of approximately −40 mmHg to −90 mmHg. This ensures a continuous air-seal around the contact area with the breast and aids with the milk extraction;

Specific travel distance 39 values for positive and negative actuation can be determined within a cycle and/or within a programme to ensure that the vacuum level within a cycle or programme oscillates within a desired vacuum range or ranges.

As indicated above, the area above the lower wall 21 between the anterior and posterior actuation areas 23,24 inside the funnel 2 is the nipple zone 45 (see FIG. 12.) where the nipple is approximately positioned during milk extraction.

As indicated above, one of the functions of the anterior actuation area 23 is the physical stimulation of the areola 17/nipple 16. The area above the anterior actuation area 23 comprises a stimulation zone 46 (see FIG. 12). The anterior actuation area 23 applies a physical stimulation on the areola 17/nipple 16 with each cycle. This locomotion of the stimulation zone 46 is biomechanical to that of the physical compression stimulation done by the infant's tongue.

In other embodiments, vibratory or other physical stimulation can be utilised to optimise fluid expression in the nursing mother through nipple, areola, breast stimulation.

Non-Nutritive Suckling Programme (NNSP)

NNSP is a biomechanical sequence to replicate an infant's non-nutritive suckling to initiate milk flow. This is a suckling profile responsible for triggering the Milk Ejection Reflex (MER). NNSP can be characterised by a vacuum range, approximately 60-90 mmHg. This range is lower than that of the Nutritive Suckling Programme (NSP) range. The suckling cycle is approximately 2 Hz. A possible set of NNSP cycles would be usually maintained until milk starts to flow into the funnel 2 at which point the programme would switch to the NSP.

Nutritive Suckling Programme (NSP)

NSP, similarly to NNSP, is a biomimetic sequence of actuation designed to replicate that of an infant's suckling cycle during milk extraction. The frequency of the cycle in NSP is less than that of NNSP and is around 1 Hz. Peak sub-atmospheric pressure levels are also higher in NSP at approximately 190-270 mmHg. This correlates to higher travel distance 39 values of negative actuation 42 in NSP than in NNSP, particularly at the posterior actuation area 24. In present embodiment the peak vacuum levels in the funnel 2 are between 150 mmHg and 250 mmHg, however, in other embodiments the funnel 2 can have larger inner diameter and/or larger posterior actuation area 24 or different choice of material or different shape or the combination of these to accommodate generating higher peak vacuum levels.

Milk Exit

Expressed milk from a breast continuously travels through the funnel 2 and exits through the milk discharge end 7. The positive actuation 41 of the posterior actuation area 24 drives the milk toward an exit considering that breastmilk as a fluid is virtually incompressible. Since the proximal opening lip end 6 is sealed on the breast by the baseline vacuum pressure, the breast milk can only exit through the milk discharge end 7. During operation once milk enters the funnel 2 there is a continues presence of fluid in the funnel 2 throughout the pumping session.

Two (or more) active actuation areas 23,24 can be used to recreate the complex functions of the infant's tongue during suckling by manipulating the lower floor 11. If desired, in other embodiments, additional active actuation areas can be positioned on the funnel 2 for example laterally on the funnel wall 8 to further aid or enhance the complex suckling mechanism.

The positive and negative actuation 41,42 stimulates the areola 17/nipple 16 to triggers milk flow, creates and maintains a baseline low vacuum level to secure air-seal on the breast, generates vacuum to draw milk from the breast, creates and maintains a close-to-zero-air environment inside the funnel 2, controls the vacuum oscillation and positions the nipple 16. The breast pump mechanism 1 of the invention therefore replicates the full range of complex functions of the infant's tongue during suckling, characterised by positive and negative actuation 41,42 of the anterior and posterior actuation areas 23,24 or other defined areas of actuation, e.g. the lateral active actuation areas described above, to further aid or enhance the functions of the suckling mechanism. This manipulation is definable by the control and sequencing of identified key variables selectable from the group comprising or consisting of but not limited to: origin point of the active actuation areas 23,24; travel distance 38 of the active actuation areas 23,24 along the trajectory of actuation; travel direction of the active actuation areas 23,24; angle of travel of the active actuation areas 23,24; actuation sequence of the active actuation areas 23,24 independently and in relation to each other; frequency, velocity, acceleration, deceleration and timing of one suckling cycle within a suckling programme, and frequency, velocity, acceleration, deceleration and timing of a single actuation within one suckling cycle.

As described above, the breast pump mechanism 1 of the invention is therefore adapted to replicate the full range of complex functions of the infant's tongue during suckling by a controlled sequencing of the anterior and posterior actuation areas 23,24.

The breast pump mechanism 1 of the invention is operable by a microcomputer having a processor coupled to memory and interface containing instructions that when executed by the processor cause the processor to activate/deactivate predefined sucking programmes or cycles (the latch, nutritive and non-nutritive suckling programmes described above and any additional predefined programs).

The microcomputer can activate and deactivating specific suckling cycles or programmes based on data continuously received by at least one sensor coupled with the funnel 2 and has data storage capabilities to enable the invention to save preferred user settings, sensor data and other useful data.

In addition to replicating the full range of complex functions of the infant's tongue during suckling such as latch, NS and NNS described above, alternative sequences can be written by changing the key variables controlling the actuator 3 to further aid or enhance these functions. For example, increasing velocity or vacuum levels and altering the values of the key variables described above the anterior actuation area 23 could increase intensity of stimulation thereby reducing time to milk ejection reflex (MER). Many other enhancements are achievable with such programming. This highly adaptive system allows for personalised programs to be created for individual users to maximise efficiency and comfort.

If desired, the invention can be configured to automatically transition between NSP and NNSP or other programmes multiple times throughout a single pumping session. Full system control is available to the user to control, adjust and select programmes. The system's smart capabilities allow configuration variability based on feedback from various sensors which can be coupled with the funnel 2, including heat sensors, motion sensors, pressure sensors, flow sensors etc.

In some embodiments, at least one of the operational and/or sensed parameters can be output or transmitted to other devices which can be used to modify at least one operational setting based upon the operational or sensed parameters. If desired, sensed parameters can also be stored and uploaded to an app-based or internet-based platform.

Figure 25:
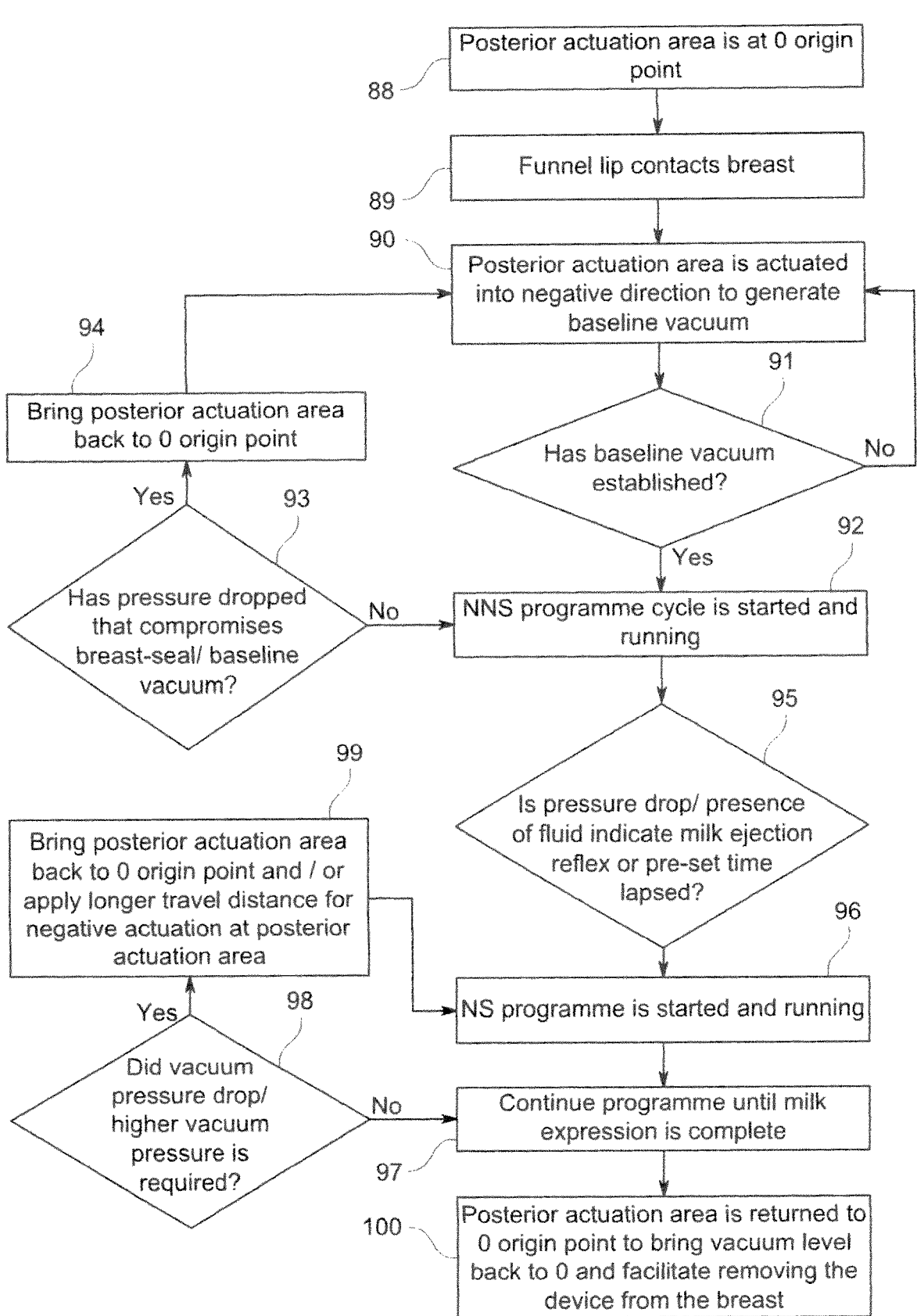
FIG. 25 is a flow-diagram describing the operation of the breast pump of the invention.

FIG. 25 is a flow-diagram summarising the operation of the breast pump of the invention outlined above. As shown in the drawing, it is first ensured that the posterior actuation area 24 is at 0 origin point 88. The funnel lips 14 are then contacted with the breast and the posterior actuation area 24 is actuated into a negative direction (a pull force) to generate baseline vacuum 90. If the baseline vacuum is not established 91 actuation of the posterior actuation area 24 is repeated 90. If the baseline vacuum is established 91, the NNS programme cycle is started and run 92.

It should be noted that if pressure drops to an extent that can compromise breast-seal/baseline vacuum 93, the posterior actuation area is retuned to 0 origin point 94.

If a pressure drop/presence of fluid indicates a milk ejection reflex or if a pre-set time has elapsed 95, the NS programme is started and run 96 and the programme is continued until milk expression is complete 97. Simultaneously, it is determined if there is a vacuum pressure drop or whether a higher vacuum pressure is required 98. If not, the programme continues as normal 96. However, if a pressure drop is detected or higher vacuum pressure is required 98, the posterior actuation area 24 is brought back to 0 origin point and/a longer travel distance is applied 99 for negative actuation at the posterior actuation area 24. The posterior actuation area 24 is then returned to 0 origin point 100 to bring the vacuum level back to 0 and facilitate removal of the breast pump 1 from the breast 98.

The invention claimed is:

1. A biomechanical breast pump (1) for expressing breast-milk comprising:

a biomimetic funnel (2) formed from a deformable body (4) having a lip end (6), a milk discharge end (7) and a wall extending (8) between the lip end (6) and the discharge end (7);

at least two active actuation areas (23,24) on the deformable body (4) configured to mimic an infant's complex suckling function;

a stationary actuation area (25) on the deformable body (4) configured to stop a hard palate (10) defined in the deformable body (4) from deforming in response to movement of the active actuation areas (23,24), and an actuator or actuators (3) for actuating the active actuation areas (23,24) wherein the active actuation areas (23,24) are separately, independently and simultaneously actuatable by the actuator or actuators (3) to exert a positive push actuation force on the deformable body (4) and a negative pull actuation force on the deformable body (4) to generate a vacuum with the funnel (2).

2. A biomechanical breast pump (1) as claimed in claim 1 wherein the active actuation areas (23,24) are provided on a lower soft floor (21) of the deformable body (4) and the stationary actuation area (25) is provided at an oppositely disposed relatively hard upper palate (10) of the deformable body (4).

3. A biomechanical breast pump (1) as claimed in claim 1 wherein the deformable body (4) defines lips (14) and a nipple chamber (22) fluidly communicable with the lips (14) to mimic the geometry of an infant's oral cavity.

4. A biomechanical breast pump (1) as claimed in claim 3 wherein the active actuation areas (23,24) comprise an anterior actuation area (23) disposed towards the lip end (6) and a posterior actuation area (24) disposed towards the milk discharge end (7).

5. A biomechanical breast pump (1) as claimed in claim 4 wherein the anterior actuation area (23) is configured to stimulate the areola (17) and/or the nipple (16) of a user and to keep the nipple (16) in position.

6. A biomechanical breast pump (1) as claimed in claim 1 wherein a positive actuation force and a negative actuation force on the active actuation areas (23,24) are actuatable by the actuator or actuators (3) in response to instructions from a controller in accordance with key variables selected from the group consisting of origin point (38) of the active actuation areas (23,24); travel distance (39) of the active actuation areas (23,24) along the trajectory of actuation; travel direction (40) positive or negative; travel direction of the active actuation areas (23,24); angle of travel of the active actuation areas (23,24); actuation sequence of the active actuation areas (23,24) independently and in relation to each other; frequency, velocity, acceleration, deceleration and timing of one suckling cycle within a suckling programme, and frequency, velocity, acceleration, deceleration and timing of a single actuation within one suckling cycle.

7. A biomechanical breast pump (1) as claimed in claim 4 wherein the breast pump (1) comprises an anterior actuation body (27) and a posterior body (28) positionally corresponding with the anterior and posterior active actuation areas (23,24) for connecting drivetrains (29,30) to the anterior and posterior active actuation areas (23,24) and the anterior and posterior actuation bodies (27,28) optionally comprise inserts or overmoulds (81).

8. A biomechanical breast pump (1) as claimed claim 1 wherein the funnel wall (8) comprises an anatomical and/or a suckling replicator (36) and/or a fluid discharge enhancer (65).

9. A biomechanical breast pump (1) as claimed in claim 3 wherein the funnel (2) comprises a nipple chamber reinforcer (71) and/or a nipple mouth reinforcer (73) and/or a lip reinforcer (74) and/or a discharge end reinforcer (102) and/or a structural reinforcer (37), the structural reinforcer comprising a side reinforcer (69) on the funnel wall (8), the side reinforcer (69) optionally comprising an elongate slit (70), the side reinforcer (69) being movable between a flexed open and a flexed closed position about the slit (70).

10. A biomechanical breast pump (1) as claimed in claim 8 wherein the fluid discharge enhancer (65) comprises a milk driving replicator (67) on the internal funnel wall (8).

11. A biomechanical breast pump (1) as claimed in claim 8 wherein the anatomical and/or suckling replicator (36) is formed by protrusions in the funnel wall (8).

12. A biomechanical breast pump (1) as claimed in claim 1 wherein the actuator (3) comprises a two-way actuator and/or a manually operated actuator (3).

* * * * *